US009018361B2

(12) United States Patent
Hickman et al.

(10) Patent No.: US 9,018,361 B2
(45) Date of Patent: Apr. 28, 2015

(54) ISOLATION AND PURIFICATION OF ANTIBODIES USING PROTEIN A AFFINITY CHROMATOGRAPHY

(71) Applicant: AbbVie Inc., North Chicago, IL (US)

(72) Inventors: Robert K. Hickman, Worcester, MA (US); Qing Huang, Singapore (SG); Cheryl L. Weed, Scituate, RI (US); Scott T. Ennis, South Grafton, MA (US); Barbara Perilli-Palmer, Bolton, MA (US); Min Wan, Frederick, MD (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/226,636

(22) Filed: Mar. 26, 2014

(65) Prior Publication Data

US 2014/0255423 A1 Sep. 11, 2014

Related U.S. Application Data

(63) Continuation of application No. 12/582,506, filed on Oct. 20, 2009, now Pat. No. 8,895,709.

(60) Provisional application No. 61/196,753, filed on Oct. 20, 2008.

(51) Int. Cl.
    *C07K 16/24* (2006.01)
    *C07K 1/16* (2006.01)
    *C07K 16/00* (2006.01)

(52) U.S. Cl.
    CPC ............... *C07K 16/00* (2013.01); *C07K 1/165* (2013.01); *C07K 16/241* (2013.01); *C07K 16/244* (2013.01); *Y10S 436/824* (2013.01)

(58) Field of Classification Search
    None
    See application file for complete search history.

(56) References Cited

U.S. PATENT DOCUMENTS

| | | | |
|---|---|---|---|
| 5,045,468 A | 9/1991 | Darfler | |
| 5,096,816 A | 3/1992 | Maiorella | |
| 5,110,913 A | 5/1992 | Coan et al. | |
| 5,429,746 A * | 7/1995 | Shadle et al. | 210/635 |
| 5,641,870 A | 6/1997 | Rinderknecht et al. | |
| 5,705,364 A | 1/1998 | Etcheverry et al. | |
| 5,721,121 A | 2/1998 | Etcheverry et al. | |
| 5,811,299 A | 9/1998 | Renner et al. | |
| 5,853,714 A | 12/1998 | Deetz et al. | |
| 5,976,833 A | 11/1999 | Furukawa et al. | |
| 6,048,728 A | 4/2000 | Inlow et al. | |
| 6,127,526 A | 10/2000 | Blank | |
| 6,399,381 B1 | 6/2002 | Blum et al. | |
| 6,528,286 B1 | 3/2003 | Ryll | |
| 6,693,173 B2 | 2/2004 | Mamidi et al. | |
| 6,870,034 B2 | 3/2005 | Breece et al. | |
| 6,914,128 B1 | 7/2005 | Salfeld et al. | |
| 6,955,917 B2 | 10/2005 | Alred et al. | |
| 6,974,681 B1 | 12/2005 | McGrew | |
| 7,074,404 B2 | 7/2006 | Basey et al. | |
| 7,122,641 B2 | 10/2006 | Vedantham et al. | |
| 7,208,585 B2 | 4/2007 | Fong et al. | |
| 7,332,303 B2 | 2/2008 | Schilling et al. | |
| 7,390,660 B2 | 6/2008 | Behrendt et al. | |
| 7,429,491 B2 | 9/2008 | Luan et al. | |
| 7,485,704 B2 | 2/2009 | Fahrner et al. | |
| 7,521,210 B2 | 4/2009 | Knudsen | |
| 7,645,609 B2 | 1/2010 | Follstad | |
| 7,714,122 B2 | 5/2010 | Nix et al. | |
| 7,820,799 B2 | 10/2010 | Godavarti et al. | |
| 7,947,471 B2 | 5/2011 | Knudsen | |
| 7,972,835 B2 | 7/2011 | Hitosugi et al. | |
| 8,058,407 B2 | 11/2011 | Sun et al. | |
| 8,067,182 B2 | 11/2011 | Kelley et al. | |
| 8,093,364 B2 | 1/2012 | Gagnon | |
| 8,163,551 B2 | 4/2012 | Alley et al. | |
| 8,192,951 B2 | 6/2012 | Wang et al. | |
| 8,209,132 B2 | 6/2012 | Bosques et al. | |
| 8,350,013 B2 | 1/2013 | Sun | |
| 8,361,797 B2 | 1/2013 | Osborne et al. | |
| 8,435,527 B2 | 5/2013 | Yumioka et al. | |
| 8,491,904 B2 * | 7/2013 | Hickman | 424/145.1 |
| 2002/0045207 A1 | 4/2002 | Krummen et al. | |
| 2003/0050450 A1 | 3/2003 | Coffman et al. | |

(Continued)

FOREIGN PATENT DOCUMENTS

| | | |
|---|---|---|
| EP | 1745141 B1 | 1/2010 |
| EP | 2357250 A2 | 8/2011 |

(Continued)

OTHER PUBLICATIONS

Aldington et al., "Scale-up of monoclonal antibody purification processes," Journal of chromatography B: biomedical Sciences & Applications, Elsevier, Amsterdam, NL, vol. 848, No. 1, 12, Mar. 2007, pp. 64-78.
Brorson Kurt et al., "Bracketed generic inactivation of rodent retroviruses by low pH treatment for monoclonal antibodies and recombinant proteins," Biotechnology and Bioengineering, May 5, 2003, vol. 82, No. 3, pp. 321-329.
Chapman, et al., "PEGylated Antibodies and Antibody Fragments for Improved Therapy: A Review", Advanced Drug Delivery Reviews, 54:531-545 (2002).
Follman et al., "Factorial screening of antibody purification processes using three chromatography steps without protein A," Journal of chromatography A 20040123 NL, vol. 1024, No. 1-2, 23, Jan. 23, 2004, pp. 79-85.
Guse et al., "purification and analytical characterization of an anti-CD4 monoclonal antibody for human therapy," Journal of chromatography A 1994 NL, vol. 661, No. 1-2, 1994, pp. 13-23.

(Continued)

*Primary Examiner* — Galina Yakovleva
(74) *Attorney, Agent, or Firm* — Foley Hoag LLP

(57) ABSTRACT

Disclosed herein are methods for the isolation and purification of antibodies wherein the use of an affinity chromatographic step results in an antibody composition sufficiently pure for pharmaceutical uses. The methods described herein comprise pH viral reduction/inactivation, ultrafiltration/diafiltration, affinity chromatography, preferably Protein A affinity, ion exchange chromatography, and hydrophobic chromatography. Further, the present invention is directed toward pharmaceutical compositions comprising one or more antibodies of the present invention.

13 Claims, 12 Drawing Sheets

(56) References Cited

U.S. PATENT DOCUMENTS

| | | | |
|---|---|---|---|
| 2003/0096414 A1 | 5/2003 | Ciccarone et al. | |
| 2003/0157108 A1 | 8/2003 | Presta | |
| 2003/0175884 A1 | 9/2003 | Umana et al. | |
| 2003/0201229 A1 | 10/2003 | Siwak et al. | |
| 2004/0033562 A1 | 2/2004 | Miller | |
| 2004/0092719 A1 | 5/2004 | Birck-Wilson et al. | |
| 2004/0132140 A1 | 7/2004 | Satoh et al. | |
| 2004/0162414 A1 | 8/2004 | Santora et al. | |
| 2004/0214289 A1 | 10/2004 | deVries et al. | |
| 2005/0107594 A1 | 5/2005 | Sun et al. | |
| 2006/0134805 A1 | 6/2006 | Berg et al. | |
| 2007/0004009 A1 | 1/2007 | Dixit et al. | |
| 2007/0072307 A1* | 3/2007 | Godavarti et al. | 436/518 |
| 2007/0110743 A1 | 5/2007 | Drapeau et al. | |
| 2007/0111284 A1 | 5/2007 | Ryll | |
| 2007/0161084 A1 | 7/2007 | Crowell et al. | |
| 2007/0178099 A1 | 8/2007 | Feldmann et al. | |
| 2007/0184529 A1 | 8/2007 | Etcheverry et al. | |
| 2007/0190057 A1 | 8/2007 | Wu et al. | |
| 2007/0213513 A1 | 9/2007 | Van Alstine et al. | |
| 2007/0292442 A1 | 12/2007 | Wan et al. | |
| 2008/0219952 A1 | 9/2008 | Fischer et al. | |
| 2008/0269132 A1 | 10/2008 | Gomes et al. | |
| 2008/0269468 A1 | 10/2008 | Vogel et al. | |
| 2008/0274507 A1 | 11/2008 | Gomes et al. | |
| 2008/0311078 A1 | 12/2008 | Gokarn et al. | |
| 2009/0053786 A1 | 2/2009 | Kao et al. | |
| 2009/0068705 A1 | 3/2009 | Drapeau et al. | |
| 2009/0142828 A1 | 6/2009 | Bucciarelli et al. | |
| 2009/0203055 A1 | 8/2009 | Ngantung et al. | |
| 2009/0208500 A1 | 8/2009 | Joly et al. | |
| 2009/0291062 A1 | 11/2009 | Fraunhofer et al. | |
| 2010/0104563 A1 | 4/2010 | Ghayer et al. | |
| 2010/0111853 A1 | 5/2010 | Hickman et al. | |
| 2010/0135987 A1* | 6/2010 | Hickman et al. | 424/130.1 |
| 2010/0136025 A1 | 6/2010 | Hickman et al. | |
| 2010/0150864 A1 | 6/2010 | Hickman et al. | |
| 2010/0190961 A1 | 7/2010 | Eon-Duval et al. | |
| 2010/0221823 A1 | 9/2010 | McCoy et al. | |
| 2010/0234577 A1 | 9/2010 | Mazzola et al. | |
| 2010/0256336 A1 | 10/2010 | Yuk et al. | |
| 2011/0003338 A1 | 1/2011 | Bayer et al. | |
| 2011/0053223 A1 | 3/2011 | Bayer et al. | |
| 2011/0053265 A1 | 3/2011 | Follstad et al. | |
| 2011/0081679 A1 | 4/2011 | Jing et al. | |
| 2011/0086798 A1 | 4/2011 | Sethuraman et al. | |
| 2011/0097336 A1 | 4/2011 | Wu et al. | |
| 2011/0130544 A1 | 6/2011 | Ram et al. | |
| 2011/0207676 A1 | 8/2011 | Callewaert et al. | |
| 2011/0213126 A1 | 9/2011 | Gonzalez et al. | |
| 2011/0236391 A1 | 9/2011 | Mahler et al. | |
| 2012/0015438 A1 | 1/2012 | Schilling et al. | |
| 2012/0039908 A1 | 2/2012 | Combs et al. | |
| 2012/0053324 A1 | 3/2012 | Kale | |
| 2012/0053325 A1 | 3/2012 | Gronke et al. | |
| 2012/0077963 A1 | 3/2012 | Hongo et al. | |
| 2012/0122759 A1 | 5/2012 | Brown et al. | |
| 2012/0149878 A1 | 6/2012 | Gillespie et al. | |
| 2012/0183997 A1 | 7/2012 | Alley et al. | |
| 2012/0190005 A1 | 7/2012 | Schaub et al. | |
| 2012/0208986 A1 | 8/2012 | Wenger et al. | |
| 2012/0277165 A1 | 11/2012 | Collins et al. | |
| 2012/0282419 A1 | 11/2012 | Ahn et al. | |
| 2012/0283416 A1 | 11/2012 | Frauenschuh et al. | |
| 2012/0283419 A1 | 11/2012 | Thiyagarajan et al. | |
| 2013/0041139 A1 | 2/2013 | Brown et al. | |
| 2013/0065224 A1 | 3/2013 | Tsang et al. | |
| 2013/0084605 A1 | 4/2013 | Zhou et al. | |
| 2013/0096283 A1 | 4/2013 | Khetan et al. | |

FOREIGN PATENT DOCUMENTS

| | | |
|---|---|---|
| EP | 1851305 B1 | 1/2012 |
| EP | 2144929 B1 | 1/2012 |
| EP | 2080809 B1 | 2/2012 |
| EP | 2152856 B1 | 8/2012 |
| EP | 2495307 A1 | 9/2012 |
| EP | 2528002 A2 | 11/2012 |
| EP | 2213726 B1 | 12/2012 |
| EP | 2574677 A1 | 4/2013 |
| WO | WO-95/22389 A1 | 8/1995 |
| WO | WO-98/17786 A1 | 4/1998 |
| WO | WO-99/18130 A1 | 4/1999 |
| WO | WO-99/032605 A1 | 7/1999 |
| WO | WO-01/58956 A2 | 8/2001 |
| WO | WO-03/045995 A2 | 6/2003 |
| WO | WO-2004/008100 A2 | 1/2004 |
| WO | WO-2004/026427 A2 | 4/2004 |
| WO | WO-2004/058800 A2 | 7/2004 |
| WO | WO-2006/110277 A1 | 10/2006 |
| WO | WO-2006/138553 A2 | 12/2006 |
| WO | WO-2007/087384 A2 | 8/2007 |
| WO | WO-2007/117490 A2 | 10/2007 |
| WO | WO-2008/068879 A1 | 6/2008 |
| WO | WO-2008/079280 A1 | 7/2008 |
| WO | WO-2008/121616 A2 | 10/2008 |
| WO | WO-2008/135498 A2 | 11/2008 |
| WO | WO-2009/023562 A2 | 2/2009 |
| WO | WO-2009/058769 A1 | 5/2009 |
| WO | WO-2009/058812 A1 | 5/2009 |
| WO | WO-2010/036443 A1 | 4/2010 |
| WO | WO-2010/072381 A1 | 7/2010 |
| WO | WO-2010/080062 A1 | 7/2010 |
| WO | WO-2010/120739 A1 | 10/2010 |
| WO | WO-2010/122460 A1 | 10/2010 |
| WO | WO-2011/005773 A2 | 1/2011 |
| WO | WO-2011/009623 A1 | 1/2011 |
| WO | WO-2011/015926 A1 | 2/2011 |
| WO | WO-2011/024025 A1 | 3/2011 |
| WO | WO-2011/031397 A1 | 3/2011 |
| WO | WO-2011/044180 A1 | 4/2011 |
| WO | WO-2011/069056 A2 | 6/2011 |
| WO | WO-2011/081898 A1 | 7/2011 |
| WO | WO-2011/127322 A1 | 10/2011 |
| WO | WO-2011/134919 A2 | 11/2011 |
| WO | WO-2011/134920 A1 | 11/2011 |
| WO | WO-2012/019160 A1 | 2/2012 |
| WO | WO-2012/030512 A1 | 3/2012 |
| WO | WO-2012/050175 A1 | 4/2012 |
| WO | WO-2012/062810 A2 | 5/2012 |
| WO | WO-2012/084829 A1 | 6/2012 |
| WO | WO-2012/120500 A2 | 9/2012 |
| WO | WO-2012/134987 A1 | 10/2012 |
| WO | WO-2012/140138 A1 | 10/2012 |
| WO | WO-2012/145682 A1 | 10/2012 |
| WO | WO-2012/147048 A2 | 11/2012 |
| WO | WO-2012/158551 A1 | 11/2012 |
| WO | WO-2013/006461 A1 | 1/2013 |
| WO | WO-2013/006479 A2 | 1/2013 |
| WO | WO-2013/009648 A2 | 1/2013 |
| WO | WO-2013/013013 A2 | 1/2013 |
| WO | WO-2013/057078 A1 | 4/2013 |

OTHER PUBLICATIONS

Ishihara et al., "Accelerated purification process development of monoclonal antibodies for shortening time to clinic," Journal of chromatography, Elsevier Science Publishers B.V., NL vol. 1176, No. 1-2, Nov. 7, 2007, pp. 149-156.

Johnston, et aL, "Low pH, caprylate incubation as a second viral inactivation step in the manufacture of albumin. Parametric and validation", Biological, 31(3):213-221 (2003).

Jovanovic, J., "Phosphorylation Site-Specific Antibodies as Research Tools in Studies of Native GABAA Receptors," The Dynamic Synapse: Molecular Methods in Ionotropic Receptor Biology, Chapter 4, Kittler JT, Moss SJ, editors, Boca Raton (FL): CRC Press; 2006.

Kostareva et al., "Purification of antibody heteropolymers using hydrophobic interaction chromatography," Journal of chromatography, Elsevier Science Publishers B.V., NL, vol. 1177, No. 2, Oct. 13, 2007, pp. 254-264.

Kramarczyk et al., "High-throughput screening of chromatographic separations: II. Hydrophobic interaction," Biotechnology and Bioengineering, Wiley & Sons, Hoboken, NJ, US, vol. 100, No. 4, Jul. 1, 2008, pp. 707-720.

(56) References Cited

OTHER PUBLICATIONS

Low, et al., "Future of Antibody Purification", Journal of Chromatography B, 848:48-63 (2007).

Osterman, "Chromatography of proteins and nucleic acids", Nauka, Moscow, pp. 31-34 (in Russian—Not translated in English), 1985.

Printout from an internet webpage http://www.gelifesciences.com/aptrix/upp01077.nsf/Content/Products?OpenDocument&moduleid=164726 retrieved on Apr. 16, 2012.

Printout from an internet webpage http://en.wikipedia.org/wiki/Sepharose retrieved on Apr. 16, 2012.

Singer, et al., "Genes and Genomes", Mir, Moscow, pp. 63-64 (1998) (in Russian—Not translated in English).

Tscheme, et al., "Time- and temperature-dependent activation of hepatitis C virus for low-pH-triggered entry", Journal of Virology, 80(4): 1734-1741 (2006).

Wang et al., "Non-size-based membrane chromatographic separation and analysis of monoclonal antibody aggregates," Analytical chemistry, American Chemical Society, US, vol. 78, No. 19, Oct. 1, 2006, pp. 6863-6867.

Yanf et al., "Expression and purification of recombinant human interleukin-18 protein using a yeast expression system," Protein expression and purification, vol. 62, No. 1, Nov. 2008, pp. 44-48.

International Search Report and Written Opinion for PCTIUS2009/061326; International Filing Date: Oct. 20, 2009.

International Search Report and Written Opinion for International Application No. PCT/US2009/061338; International Filing Date: Oct. 20, 2009.

International Search Report and Written Opinion for International Application No. PCT/US2009/061329; International Filing Date: Oct. 20, 2009.

International Search Report and Written Opinion for International Application No. PCT/US2009/061335; International Filing Date: Oct. 20, 2009.

Office Action Received on Nov. 19, 2013 from Russian application No. 2011120178, issued on Nov. 11, 2013 (English translation).

Office Action received on Sep. 9, 2013 from Russian application No. 2011120174, issued on Aug. 16, 2013 (English translation).

Iyer, H. et al., "Considerations During Development of a Protein A-Based Antibody Purification Process," BioPharm, Jan. 2002.

Pease, L.F. et al., "Determination of Protein Aggregation With Differential Mobility Analysis: Application to IgG Antibody," Biotechnology and Bioengineering, 101(6):1214-1222 (2008).

Thies, M.J.W. et al., "The Alternatively Folded State of the Antibody CH3 Domain," J. Mol. Biol., 309:1077-1085 (2001).

van Erp, R. et al., "Monitoring of the Production of Monoclonal Antibodies by Hybridomas. Part II: Characterization and Pruification of Acid Proteases Present in Cell Culture Supernatant," J. Biotechnology, 20:249-261 (1991).

Phillips, J. et al. "Manufacture and quality control of CAMPATH-1 antibodies for clinical trials" Cytotherapy 3(3):233-242 (2001).

* cited by examiner

Figure 1.

- Anti-IL-12 Antibody (ABT-874) Heavy Chain Variable Region Sequence

```
1          10         20         30         40
QVQLVESGGG VVQPGRSLRL SCAASGFTFS SYGMHWVRQA
                                 CDR1

PGKGLEQVAF IRYDGSNKYY ADSVKGRFTI SRDNSKNTLY
           CDR2

LQMNSLRAED TAVYYCKTHG SHDNWGQGTM VTVSS
                CDR3
```

- Anti-IL-12 Antibody (ABT-874) Light Chain Variable Region Sequence

```
1          10         20         30         40
QSVLTQPPSV SGAPGQRVTI SCSGSRSNIG SNTVKWYQQL
                      CDR1

PGTAPKLLIY YGNDQRPSGV PDRFSGSKGT SASLAITGVQ
           CDR2

AEDEADYYCQ SYDRYTHPAL LFGTGTKVTVLG
          CDR3
```

Figure 2.

- Anti-IL-18 Antibody (ABT-325) Heavy Chain Sequence

```
1          10         20         30         40         50
EVQLVQSGTE VKKPGESLKI SCKGSGYTVT SYWIGWVRQM PGKGLEWMGF

IYPGDSETRY SPTFQGQVTI SADKSFNTAF LQWSSLKASD TAMYYCARVG

SGWYPYTFDI WGQGTMVTVS SASTKGPSVF PLAPSSKSTS GGTAALGCLV

KDYFPEPVTV SWNSGALTSG VHTFPAVLQS SGLYSLSSVV TVPSSSLGTQ

TYICNVNHKP SNTKVDKKVE PKS
```

- Anti-IL-18 Antibody (ABT-325) Light Chain Sequence

```
1          10         20         30         40         50
EIVMTQSPAT LSVSPGERAT LSCRASESIS SNLAWYQQKP GQAPRLFIYT

ASTRATDIPA RFSGSGSGTE FTLTISSLQS EDFAVYYCQQ YNNWPSITFG

QGTRLEIKRT VAAPSVFIFP PSDEQLKSGT ASVVCLLNNF YPREAKVQWK

VDNALQSGNS QESVTEQDSK DSTYSLSSTL TLSKADYEKH KVYACEVTHQ

GLSSPVTKSF NRGE
```

Figure 3.

- Anti-TNFα Antibody (Adalimumab) Heavy Chain Variable Region Sequence

```
1          10         20         30         40         50
EVQLVESGGG LVQPGRSLRL SCAASGFTFD DYAMHWVRQA PGKGLEWVSA
                                 CDR1

ITWNSGHIDY ADSVEGRFTI SRDNAKNSLY LQMNSLRAED TAVYYCAKVS
   CDR2

YLSTASSLDY WGQGTLVTVS S
   CDR3
```

- Anti-TNFα Antibody (Adalimumab) Light Chain Variable Region Sequence

```
1          10         20         30         40         50
DIQMTQSPSS LSASVGDRVT ITCRASQGIR NYLAWYQQKP GKAPKLLIYA
                        CDR1

ASTLQSGVPS RFSGSGSGTD FTLTISSLQP EDVATYYCQR YNRAPYTFGQ
CDR2                                        CDR3

GTKVEIK
```

Figure 4. Chromatogram of MabSelect™ column at 300 L bioreactor scale
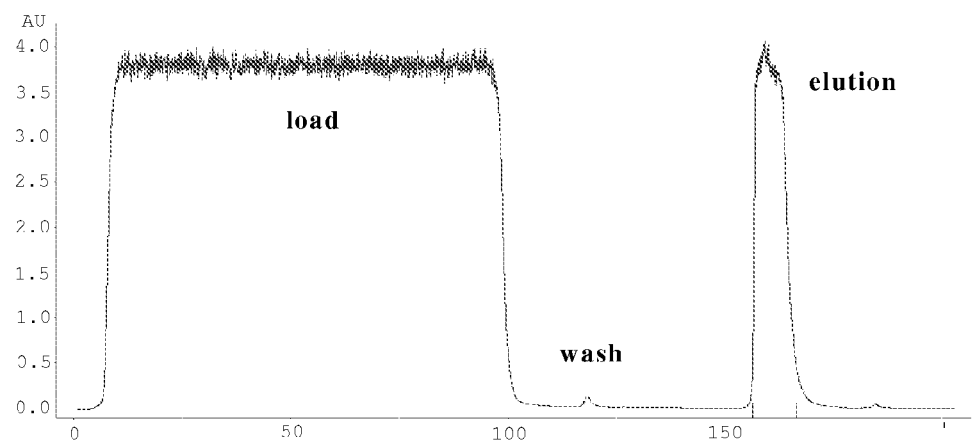
Data presented as absorbance (280 nm) versus elution volume.

Figure 5.    Evaluation of MabSelect™ Wash Conditions
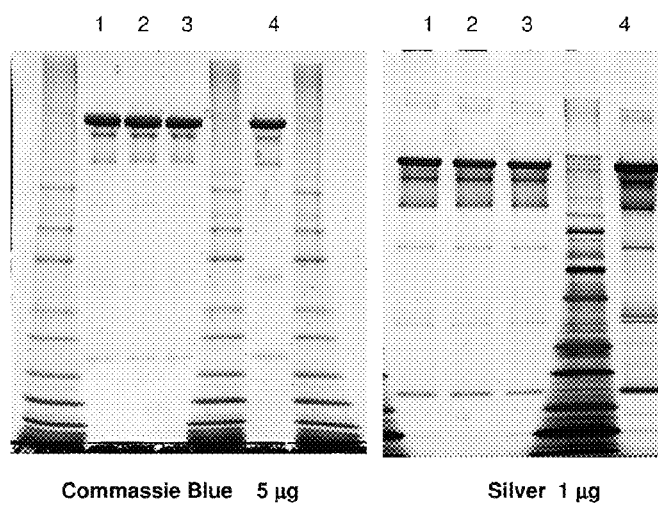
Lanes 1, 2 and 3 were eluted Ab with no wash, 0.5 M NaCl wash or 20 mM citrate, 0.5 M NaCl wash at pH 6, respectively. Lane 4 was wash with 20 mM citrate, 0.5 M NaCl, pH 6 buffer.

Figure 6. SDS-PAGE of pH 8 7ms/cm Precipitates
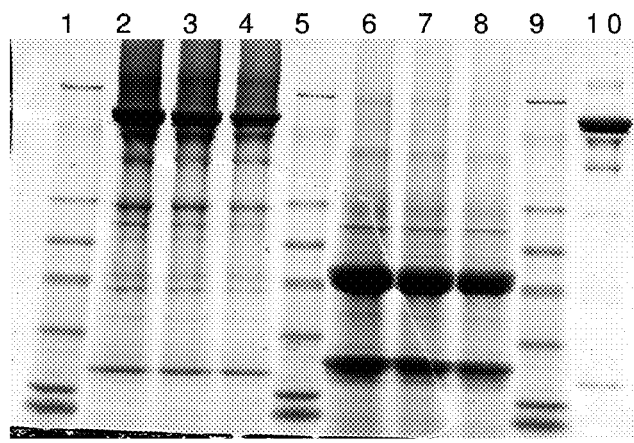
Lanes 1, 5 and 9 are molecular weight standard. Lanes 2, 3 and 4 are precipitates formed at pH 8 and 7 mS/cm (non-reduced). Lanes 6, 7 and 8 are precipitate formed at pH 8 and 7 mS/cm (reduced). Lane 10 is the MabSelect™ eluate.

Figure 7. Flow-Through Wash Profile of 300 L Bioreactor Scale Q Sepharose™ FF Chromatography Column
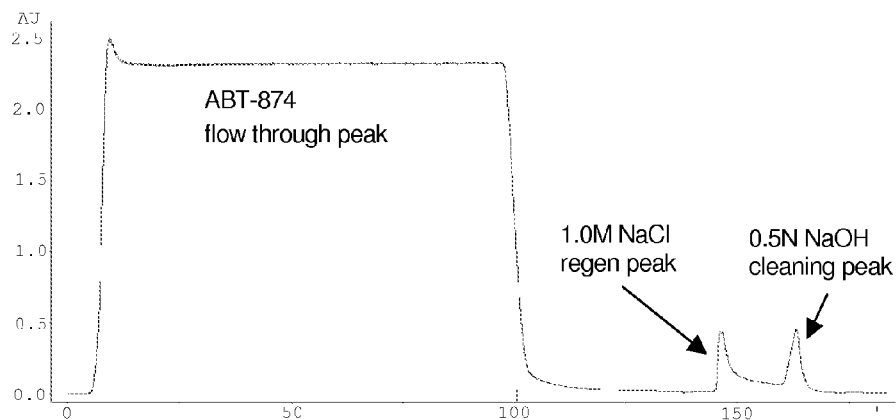
Data are presented as absorbance (280 nm) versus process volume

Figure 8. Elution Profile of 300 L Bioreactor Scale Phenyl Sepharose™ HP Chromatography Column
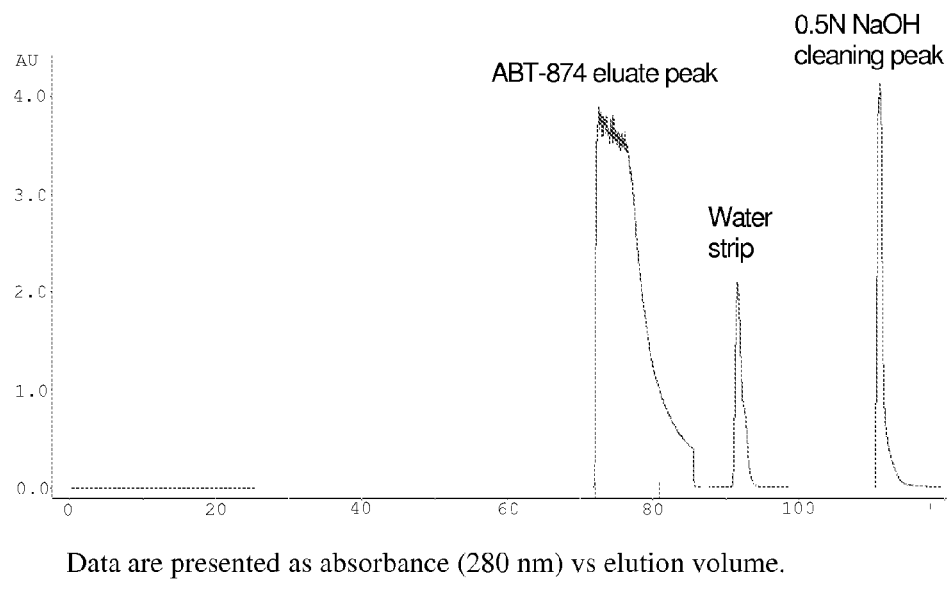
Data are presented as absorbance (280 nm) vs elution volume.

Figure 9.     Antibody Binding Breakthrough Curve in MabSelect™
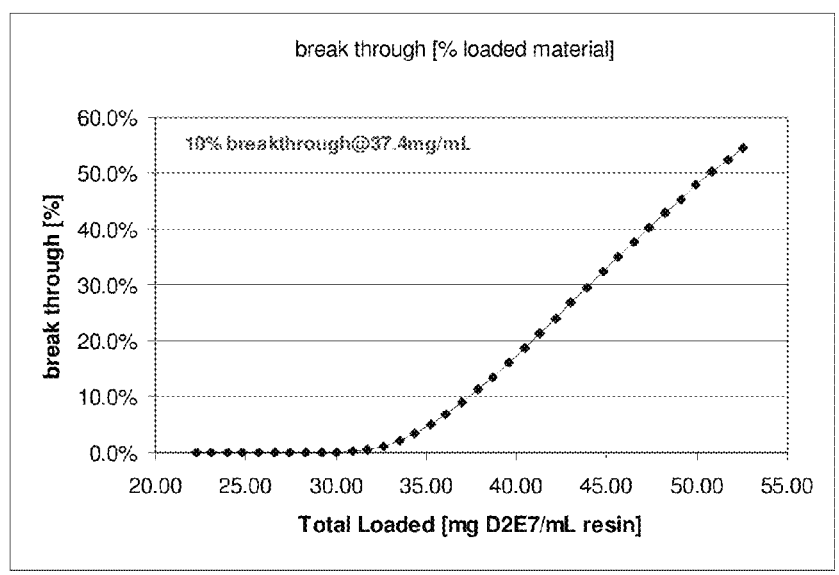
Material: AY-04 Lot 35205BI clarified antibody harvest
Load: pH7, 400 cm/hr
Column size: 1.6 x 5 cm

Figure 10.   SDS-PAGE of Protein A Process Run and AY-04
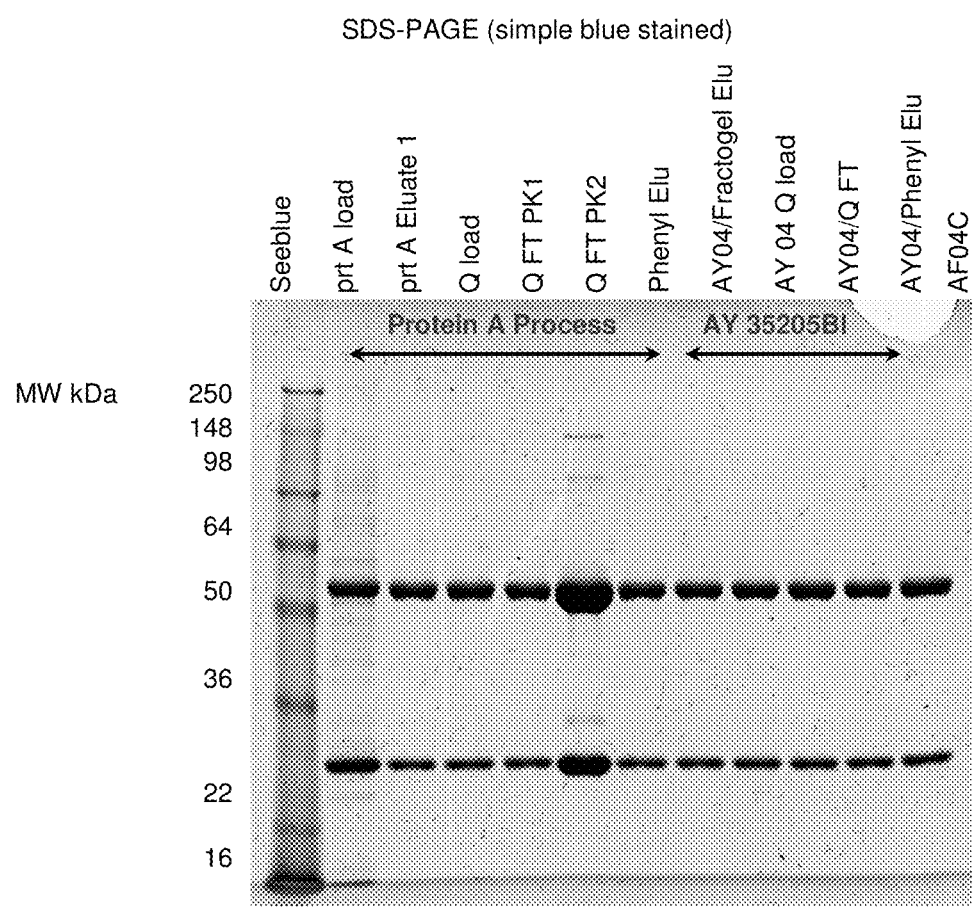

Figure 11. MabSelect™ Adalimumab Recovery Yield vs. Elutin pH
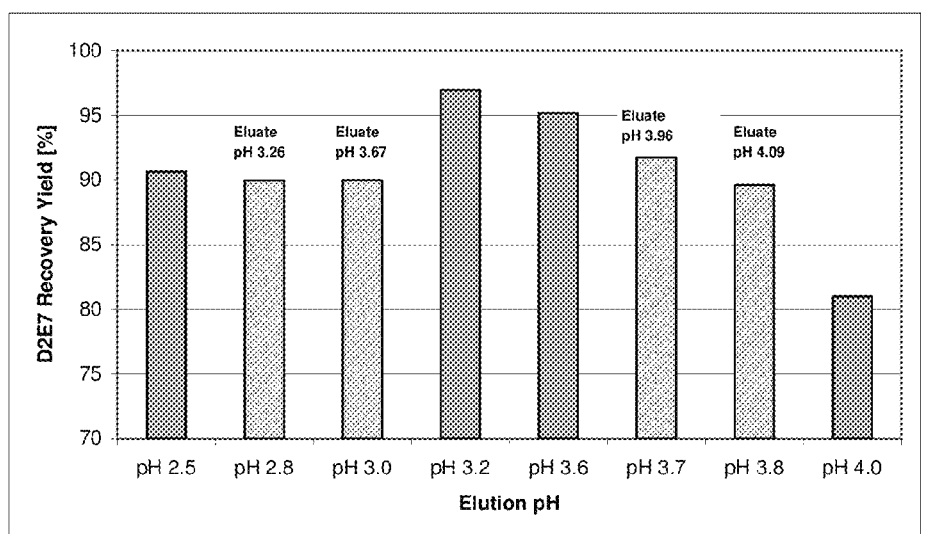
Material: AY-04 Lot 35205BI clarified antibody harvest
Load: pH7, 400 cm/hr
Column size: 1.6 x 5 cm

Figure 12. Antibody (or Adalimumab) Monomer vs. Elution pH & Incubation Time
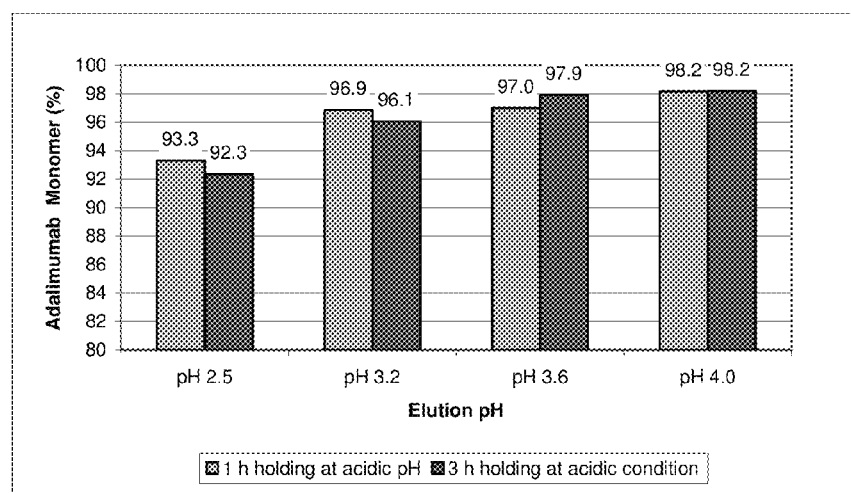

SEQUENCE LISTING

```
<160> NUMBER OF SEQ ID NOS: 6

<210> SEQ ID NO 1
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 1
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Gln Val
        35                  40                  45

Ala Phe Ile Arg Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115
```

<210> SEQ ID NO 2
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 2

```
Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Gly Asn Asp Gln Arg Pro Ser Gly Val Pro Asp Arg Phe
50                  55                  60

Ser Gly Ser Lys Gly Thr Ser Ala Ser Leu Ala Ile Thr Gly Val Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110
```

<210> SEQ ID NO 3
<211> LENGTH: 223
<212> TYPE: PRT
<213> ORGANISM: Artificial sequence
<220> FEATURE:
<223> OTHER INFORMATION: Synthetic polypeptide

<400> SEQUENCE: 3

```
Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Thr Val Thr Ser Tyr
            20                  25                  30

Trp Ile Gly Trp Val Arg Gln Met Pro Gly Lys Gly Leu Glu Trp Met
        35                  40                  45

Gly Phe Ile Tyr Pro Gly Asp Ser Glu Thr Arg Tyr Ser Pro Thr Phe
50                  55                  60

Gln Gly Gln Val Thr Ile Ser Ala Asp Lys Ser Phe Asn Thr Ala Phe
```

```
                 65                  70                  75                  80
Leu Gln Trp Ser Ser Leu Lys Ala Ser Asp Thr Ala Met Tyr Tyr Cys
                85                  90                  95

Ala Arg Val Gly Ser Gly Trp Tyr Pro Tyr Thr Phe Asp Ile Trp Gly
                100                 105                 110

Gln Gly Thr Met Val Thr Val Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser
                210                 215                 220

<210> SEQ ID NO 4
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 4

Glu Ile Val Met Thr Gln Ser Pro Ala Thr Leu Ser Val Ser Pro Gly
1               5                   10                  15

Glu Arg Ala Thr Leu Ser Cys Arg Ala Ser Glu Ser Ile Ser Ser Asn
                20                  25                  30

Leu Ala Trp Tyr Gln Gln Lys Pro Gly Gln Ala Pro Arg Leu Phe Ile
                35                  40                  45

Tyr Thr Ala Ser Thr Arg Ala Thr Asp Ile Pro Ala Arg Phe Ser Gly
                50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Ser
                85                  90                  95

Ile Thr Phe Gly Gln Gly Thr Arg Leu Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu
```

```
    210

<210> SEQ ID NO 5
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 5

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 6
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys
            100                 105
```

ISOLATION AND PURIFICATION OF ANTIBODIES USING PROTEIN A AFFINITY CHROMATOGRAPHY

CROSS REFERENCE TO RELATED APPLICATION

This application is a continuation of U.S. patent application Ser. No. 12/582,506, filed Oct. 20, 2009, which claims the benefit of U.S. Provisional Application Ser. No. 61/196,753, filed Oct. 20, 2008, each of which is hereby incorporated by reference in its entirety. The application also incorporates by reference the entire content of U.S. Patent Application Publication No. US 2010/0135987, published Jun. 3, 2010.

BACKGROUND OF THE INVENTION

Purification processes for pharmaceutical grade monoclonal antibodies produced by fermentation culture typically involve four basic steps. These steps include (1) harvest/clarification—separation of host cells from the fermentation culture; (2) capture—separation of antibody from the majority of components in the clarified harvest; (3) fine purification—removal of residual host cell contaminants and aggregates; and (4) formulation—place the antibody into an appropriate carrier for maximum stability and shelf life.

However, these steps often do not necessarily result in antibody compositions of sufficient purity for use in pharmaceutical contexts. There is a present need for methods of producing and purifying an antibody of interest in sufficiently pure form to be suitable for pharmaceutical use. The present invention addresses this need.

SUMMARY OF THE INVENTION

The present invention is directed to methods for isolating and purifying antibodies from a sample matrix. In certain aspects, the invention is directed to methods of antibody purification employing affinity chromatography, preferably Protein A chromatography. In specific aspects, the methods herein employ an acid inactivation step, an affinity chromatographich step, and one or more additional chromatography and/or filtration steps. The chromatography steps can include one or more step of ion exchange chromatography and/or hydrophobic interaction chromatography. Further, the present invention is directed toward pharmaceutical compositions comprising one or more antibodies purified by a method described herein.

One embodiment or the present invention is directed toward a method of purifying an antibody or antigen-binding portion thereof from a sample matrix such that the resulting antibody composition is substantially free of host cell proteins ("HCPs"). In one aspect, the sample matrix (or simply "sample") comprises a cell line harvest wherein the cell line is employed to produce specific antibodies of the present invention. In a particular aspect, the sample matrix is prepared from a cell line used to produce anti-IL-12 antibodies; in another aspect, the sample matrix is prepared from a cell line used to produce anti-TNFα antibodies; and in another aspect the sample matrix is prepared from a cell line used to produce anti-IL-18 antibodies.

One method of the present invention involves subjecting a sample matrix comprising the putative antibody of interest or antigen-binding portion thereof to a pH adjustment. In one aspect, the pH is adjusted to an acidic pH. An example of a suitable pH is between about a pH of 3 and 5, preferably a pH of about 3.5. This primary recovery is performed, in part, to reduce or inactivate pH-sensitive viruses. In addition to reducing and/or inactivating viruses, the acidic conditions facilitate the removal of cells and cellular debris thus forming a primary recovery sample. After a suitable period of time, the pH can be adjusted toward a more neutral or basic pH and the primary recovery sample is subjected to affinity chromatography, preferably Protein A chromatography. In one aspect, the affinity chromatography sample is collected and further subjected to subsequent chromatographic steps such as ion exchange and hydrophobic interactive chromatography.

In one embodiment, the affinity chromatography step comprises subjecting the primary recovery sample to a column comprising a suitable affinity chromatographic support. Non-limiting examples of such chromatographic supports include, but are not limited to Protein A resin, Protein G resin, affinity supports comprising the antigen against which the antibody of interest was raised, and affinity supports comprising an Fc binding protein. Protein A resin is useful for affinity purification and isolation of antibodies (IgG). In one aspect, a Protein A column is equilibrated with a suitable buffer prior to sample loading. An example of a suitable buffer is a Tris/NaCl buffer, pH around 7.2. Following this equilibration, the sample can be loaded onto the column. Following the loading of the column, the column can be washed one or multiple times using, e.g., the equilibrating buffer. Other washes including washes employing different buffers can be used before eluting the column. The Protein A column can then be eluted using an appropriate elution buffer. An example of a suitable elution buffer is an acetic acid/NaCl buffer, pH around 3.5. The eluate can be monitored using techniques well known to those skilled in the art. For example, the absorbance at $OD_{280}$ can be followed. The eluated fraction(s) of interest can then be prepared for further processing.

In one embodiment, an ion exchange step follows Protein A affinity chromatography. This ion exchange step can be either cation or anion exchange or a combination of both. This step can be a single ion exchange procedure or can include multiple ion exchange steps such as a cation exchange step followed by an anion exchange step or visa versa. In one aspect, the ion exchange step is a one step procedure. In another aspect, the ion exchange step involves a two step ion exchange process. A suitable cation exchange column is a column whose stationary phase comprises anionic groups. An example of such a column is a Fractogel™ $SO_3^-$. This ion exchange capture chromatography step facilitates the isolation of antibodies from a sample. A suitable anion exchange column is a column whose stationary phase comprises cationic groups. An example of such a column is a Q Sepharose™ column. One or more ion exchange step further isolates antibodies by reducing impurities such as host cell proteins and DNA and, where applicable, affinity matrix protein. This anion exchange procedure is a flow through mode of chromatography wherein the antibodies of interest do not interact or bind to the anion exchange resin (or solid phase). However, many impurities do interact with and bind to the anion exchange resin. In a particular aspect, the ion exchange step is anion exchange chromatography.

The affinity chromatography eluate is prepared for ion exchange by adjusting the pH and ionic strength of the sample buffer. For example, the affinity eluate can be adjusted to a pH of about 6.0 to about 8.5 in a 1 M Tris buffer. Prior to loading the sample (the affinity eluate) onto the ion exchange column, the column can be equilibrated using a suitable buffer. An example of a suitable buffer is a Tris/NaCl buffer with a pH of about 6.0 to about 8. Following equilibration, the column can be loaded with the affinity eluate. Following loading, the column can be washed one or multiple times with a suitable buffer. An example of a suitable buffer is the equilibration buffer itself. Flow-through collection can commence, e.g., as the absorbance ($OD_{280}$) rises above about 0.2 AU.

In certain embodiments, the present method employs a further step. This step involves the use of hydrophobic interactive chromatography ("HIC"). A suitable column is one whose stationary phase comprises hydrophobic groups. An example of such a column is a phenyl Sepharose™ column. It is possible that the antibodies of interest have formed aggregates during the isolation/purification process. This hydrophobic chromatographic step facilitates the elimination of these aggregations. It also assists in the removal of impurities. The procedure uses a high salt buffer which promotes interaction of the antibodies (or aggregations thereof) with the hydrophobic column. The column is eluted using lower concentrations of salt.

In another embodiment, the HIC eluate is filtered using a viral removal filter such as an Ultipor DV20™ filter. This procedure separates viral particles from the phenyl eluate to reduce the amount of virus (if present) to safe levels. Filters well known to those skilled in the art can be used in this embodiment.

The purity of the antibodies of interest in the resultant sample product can be analyzed using methods well known to those skilled in the art, e.g., size-exclusion chromatography, Poros™ A HPLC Assay, HCP ELISA, Protein A ELISA, and western blot analysis.

In yet another embodiment, the invention is directed to one or more pharmaceutical compositions comprising an isolated antibody or antigen-binding portion thereof and an acceptable carrier. In another aspect, the compositions further comprise one or more pharmaceutical agents.

BRIEF DESCRIPTIONS OF THE DRAWINGS

FIG. 1 discloses the heavy (SEQ ID NO:1) and light (SEQ ID NO:2) chain variable region sequences of a non-limiting example of an anti-IL-12 antibody (ABT-847).

FIG. 2 discloses the heavy (SEQ ID NO:3) and light (SEQ ID NO:4) chain sequences of a non-limiting example of an anti-IL-18 antibody (ABT-325).

FIG. 3 discloses the heavy (SEQ ID NO:5) and light (SEQ ID NO:6) chain variable region sequences of a non-limiting example of an anti-TNFa antibody (Adalimumab).

FIG. 4 depicts a representative chromatogram from a 300 L bioreactor showing product purity after MabSelect™ Protein A chromatography was used to capture anti-IL-12 antibodies and reduce product and process related impurities such as single and double light chain fragments, CHO host cell proteins (HCPs) and DNA, etc.

FIG. 5 depicts an evaluation of MabSelect™ wash conditions.

FIG. 6 is a photograph of a polyacrylamide gel of precipitates obtained after a MabSelect™ eluate was adjusted to pH 8 and a conductivity of 7 mS/cm.

FIG. 7 depicts a representative flow-through wash profile of a 300 L bioreactor scale Q Sepharose™ FF chromatography column.

FIG. 8 depicts a representative elution profile of a 300 L bioreactor scale Phenyl Sepharose™ HP chromatography column.

FIG. 9 depicts the results of a dynamic binding capacity assay where the 10% breakthrough point for MabSelect™ resin is identified to be at 37.4 g antibody per L of resin.

FIG. 10 is a photograph of a polyacrylamide gel conducted to compare the intermediate differences between Protein A process and AY-04 process. 2 μg of antibody of each sample was loaded.

FIG. 11 depicts MabSelect™ Adalimumab Recovery Yield vs. Elutin pH. The figure demonstrates that a yield of at least 90% was obtained for an elution pH range from 2.5 to 3.8 and a significant decrease in yield occurs at pH 4.

FIG. 12 depicts the results of an assay comparing the recovery of Adalimumab monomer vs. elution pH and incubation time.

DETAILED DESCRIPTION OF THE INVENTION

The present invention is directed to methods for isolating and purifying antibodies from a sample matrix. One aspect of the invention is directed to viral reduction/inactivation of samples generated in the various steps of antibody purification. In a particular aspect, methods herein employ an acid viral reduction/inactivation step followed by one or more chromatography steps. The chromatography steps can include one or more of the following chromatographic procedures: ion exchange chromatography, affinity chromatography, and hydrophobic interaction chromatography. Further, the present invention is directed toward pharmaceutical compositions comprising one or more antibodies purified by a method described herein.

For clarity and not by way of limitation, this detailed description is divided into the following sub-portions:
1. Definitions;
2. Antibody Generation;
3. Antibody Production;
4. Antibody Purification;
5. Methods of Assaying Sample Purity;
6. Further Modifications;
7. Pharmaceutical Compositions; and
8. Antibody Uses.

1. Definitions

In order that the present invention may be more readily understood, certain terms are first defined.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., hIL-12, hTNFα, or hIL-18). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The phrase "human interleukin 12" (abbreviated herein as hIL-12, or IL-12), as used herein, includes a human cytokine that is secreted primarily by macrophages and dendritic cells. The term includes a heterodimeric protein comprising a 35 kD subunit (p35) and a 40 kD subunit (p40) which are linked together with a disulfide bridge. The heterodimeric protein is referred to as a "p70 subunit". The structure of human IL-12 is described further in, e.g., Kobayashi, et al. (1989) J. Exp Med. 170:827-845; Seder, et al. (1993) Proc. Natl. Acad. Sci. 90:10188-10192; Ling, et al. (1995) J. Exp Med. 154:116-127; Podlaski, et al. (1992) Arch. Biochem. Biophys. 294: 230-237, the entire teachings of which are incorporated herein by reference. The nucleic acid encoding IL-12 is available as GenBank Accession No. NM_000882 and the polypeptide sequence is available as GenBank Accession No. NP_000873.2. The term human IL-12 is intended to include recombinant human IL-12 (rh IL-12), which can be prepared by standard recombinant expression methods.

The phrase "human interleukin 18" (abbreviated herein as hIL-18, or IL-18), as used herein, includes a human cytokine that is initially synthesized as biologically inactive 193 amino acid precursor protein as well as the 156 amino acid mature protein produced by, for example, but not by way of limitation, cleavage of the precursor protein, e.g., by caspase-1 or caspase-4, which exhibits biological activities that include the co-stimulation of T cell proliferation, the enhancement of NK cell cytotoxicity, the induction of IFN-γ production by T cells and NK cells, and the potentiation of T helper type 1 (Th1) differentiation. The nucleic acid encoding IL-18 is available as GenBank Accession No. NM_001562 and the polypeptide sequence is available as GenBank Accession No. NP_001553. The term human IL-18 is intended to include recombinant human IL-18 (rh IL-18), which can be prepared by standard recombinant expression methods.

The phrase "human Tumor necrosis factor-α" (abbreviated herein as hTNFα or TNFα) is a multifunctional pro-inflammatory cytokine secreted predominantly by monocytes/macrophages that has effects on lipid metabolism, coagulation, insulin resistance, and endothelial function. TNFα is a soluble homotrimer of 17 kD protein subunits. A membrane-bound 26 kD precursor form of TNFα also exists. It is found in synovial cells and macrophages in tissues. Cells other than monocytes or macrophages also produce TNFα. For example, human non-monocytic tumor cell lines produce TNFα as well as CD4+ and CD8+ peripheral blood T lymphocytes and some cultured T and B cell lines produce TNFα. The nucleic acid encoding TNFα is available as GenBank Accession No. X02910 and the polypeptide sequence is available as GenBank Accession No. CAA26669. The term human TNFα is intended to include recombinant human TNFα (rh TNFα), which can be prepared by standard recombinant expression methods.

The terms "Kabat numbering", "Kabat definitions" and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) Ann. NY Acad, Sci. 190:382-391 and, Kabat, E. A., et al. (1991) Sequences of Proteins of Immunological Interest, Fifth Edition, U.S. Department of Health and Human Services, NIH Publication No. 91-3242, the entire teachings of which are incorporated herein by reference). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "selective mutagenesis approach" includes a method of improving the activity of an antibody by selecting and individually mutating CDR amino acids at least one suitable selective mutagenesis position, hypermutation, and/or contact position. A "selectively mutated" human antibody is an antibody which comprises a mutation at a position selected using a selective mutagenesis approach. In another aspect, the selective mutagenesis approach is intended to provide a method of preferentially mutating selected individual amino acid residues in the CDR1, CDR2 or CDR3 of the heavy chain variable region (hereinafter H1, H2, and H3, respectively), or the CDR1, CDR2 or CDR3 of the light chain variable region (hereinafter referred to as L1, L2, and L3, respectively) of an antibody. Amino acid residues may be selected from selective mutagenesis positions, contact positions, or hypermutation positions. Individual amino acids are selected based on their position in the light or heavy chain variable region. It should be understood that a hypermutation position can also be a contact position. In one aspect, the selective mutagenesis approach is a "targeted approach". The language "targeted approach" is intended to include a method of mutating selected individual amino acid residues in the CDR1, CDR2 or CDR3 of the heavy chain variable region or the CDR1, CDR2 or CDR3 of the light chain variable region of an antibody in a targeted manner, e.g., a "Group-wise targeted approach" or "CDR-wise targeted approach". In the "Group-wise targeted approach", individual amino acid residues in particular groups are targeted for selective mutations including groups I (including L3 and H3), II (including H2 and L1) and III (including L2 and H1), the groups being listed in order of preference for targeting. In the "CDR-wise targeted approach", individual amino acid residues in particular CDRs are targeted for selective mutations with the order of preference for targeting as follows: H3, L3, H2, L1, H1 and L2. The selected amino acid residue is mutated, e.g., to at least two other amino acid residues, and the effect of the mutation on the activity of the antibody is determined. Activity is measured as a change in the binding specificity/affinity of the antibody, and/or neutralization potency of the antibody. It should be understood that the selective mutagenesis approach can be used for the optimization of any antibody derived from any source including phage display, transgenic animals with human IgG germline genes, human antibodies isolated from human B-cells. The selective mutagenesis approach can be used on antibodies which can not be optimized further using phage display technology. It should be understood that antibodies from any source including phage display, transgenic animals with human IgG germline genes, human antibodies isolated from human B-cells can be subject to back-mutation prior to or after the selective mutagenesis approach.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hIL-12 is substantially free of antibodies that specifically bind antigens other than hIL-12). An isolated antibody that specifically binds hIL-12 may bind IL-12 molecules from other species. Moreover, an isolated antibody may be substantially free of other cellular material and/or chemicals. Suitable anti-IL-12 antibodies that may be purified in the context of the instant invention are disclosed in U.S. Pat. No. 6,914,128 (which is hereby incorporated by reference in its entirety) including, but not limited to the anti-IL-12 antibody identified in that patent as J695, and which has subsequently been identified as ABT-874. Suitable anti-IL-18 antibodies that may be purified and isolated in the context of the instant invention are disclosed in U.S. Ser. Nos. 09/780,035 and 10/988,360, including, the antibody that has subsequently been identified as ABT-325. A suitable anti-TNFα antibody is Adalimumab (Abbott Laboratories).

A "neutralizing antibody" (or an "antibody that neutralized hIL-12 activity") includes an antibody whose binding to hIL-12 results in inhibition of the biological activity of hIL-12. This inhibition of the biological activity of hIL-12 can be assessed by measuring one or more indicators of hIL-12 biological activity, such as inhibition of human phytohemagglutinin blast proliferation in a phytohemagglutinin blast proliferation assay (PHA), or inhibition of receptor binding in a human IL-12 receptor binding assay. These indicators of hIL-12 biological activity can be assessed by one or more of several standard in vitro or in vivo assays known in the art.

A "neutralizing antibody" (or an "antibody that neutralized hIL-18 activity") includes an antibody whose binding to hIL-18 results in inhibition of the biological activity of hIL-18. This inhibition of the biological activity of hIL-18 can be assessed by measuring one or more indicators of hIL-18 biological activity, such as induction of IFNγ production by T cells or NK cells, or inhibition of IL-18 receptor binding in a human IL-18 receptor binding assay. These indicators of hIL-18 biological activity can be assessed by one or more of several standard in vitro or in vivo assays known in the art.

The term "activity" includes activities such as the binding specificity/affinity of an antibody for an antigen, e.g., an anti-hIL-12 antibody that binds to an IL-12 antigen and/or the neutralizing potency of an antibody, e.g., an anti-hIL-12 antibody whose binding to hIL-12 inhibits the biological activity of hIL-12, e.g., inhibition of PHA blast proliferation or inhibition of receptor binding in a human IL-12 receptor binding assay. The term "activity" also includes activities such as the binding specificity/affinity of an anti-IL-18 antibody for its antigen, e.g., an anti-hIL-18 antibody that binds to an IL-18 antigen and/or the neutralizing potency of an antibody, e.g., an anti-hIL-18 antibody whose binding to hIL-18 inhibits the biological activity of hIL-18. The term "activity" also includes activities such as the binding specificity/affinity of an anti-TNFα antibody for its antigen, e.g., an anti-TNFα antibody that binds to a TNFα antigen and/or the neutralizing potency of an antibody, e.g., an anti-TNFα antibody whose binding to hTNFα inhibits the biological activity of hTNFα.

The phrase "surface plasmon resonance" includes an optical phenomenon that allows for the analysis of real-time biospecific interactions by detection of alterations in protein concentrations within a biosensor matrix, e.g., using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277, the entire teachings of which are incorporated herein.

The term "Koff", as used herein, is intended to refer to the off rate constant for dissociation of an antibody from the antibody/antigen complex.

The term "Kd", as used herein, is intended to refer to the dissociation constant of a particular antibody-antigen interaction.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3), e.g. those that bind hIL-12, hTNFα, or hIL-18, and includes a nucleic acid molecule in which the nucleotide sequences encoding the antibody or antibody portion are free of other nucleotide sequences encoding antibodies or antibody portions that bind antigens other than hIL-12, hTNFα, or hIL-18, which other sequences may naturally flank the nucleic acid in human genomic DNA. Thus, e.g, an isolated nucleic acid of the invention encoding a VH region of an anti-IL-12h, anti-TNFα, or anti-hIL-18 antibody contains no other sequences encoding other VH regions that bind antigens other than, for example, IL-12, hTNFα, or hIL-18. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The phrase "viral reduction/inactivation", as used herein, is intended to refer to a decrease in the number of viral particles in a particular sample ("reduction"), as well as a decrease in the activity, for example, but not limited to, the infectivity or ability to replicate, of viral particles in a particular sample ("inactivation"). Such decreases in the number and/or activity of viral particles can be on the order of about 1% to about 99%, preferably of about 20% to about 99%, more preferably of about 30% to about 99%, more preferably of about 40% to about 99%, even more preferably of about 50% to about 99%, even more preferably of about 60% to about 99%, yet more preferably of about 70% to about 99%, yet more preferably of about 80% to 99%, and yet more preferably of about 90% to about 99%. In certain non-limiting embodiments, the amount of virus, if any, in the purified antibody product is less than the ID50 (the amount of virus that will infect 50 percent of a target population) for that virus, preferably at least 10-fold less than the ID50 for that virus, more preferably at least 100-fold less than the ID50 for that virus, and still more preferably at least 1000-fold less than the ID50 for that virus The phrase "contact position" includes an amino acid position in the CDR1, CDR2 or CDR3 of the heavy chain variable region or the light chain variable region of an antibody which is occupied by an amino acid that contacts antigen in one of the twenty-six known antibody-antigen structures. If a CDR amino acid in any of the twenty-six known solved structures of antibody-antigen complexes contacts the antigen, then that amino acid can be considered to occupy a contact position. Contact positions have a higher probability of being occupied by an amino acid which contact antigens than in a non-contact position. In one aspect, a contact position is a CDR position which contains an amino acid that contacts antigen in greater than 3 of the 26 structures (>1.5%). In another aspect, a contact position is a CDR position which contains an amino acid that contacts antigen in greater than 8 of the 25 structures (>32%).

2. Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody preferably can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human)

immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies of this disclosure are human monoclonal antibodies. Such human monoclonal antibodies directed against IL-12, TNFα, or IL-18 can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure, such as anti-IL-12, anti-TNFα, or anti-IL-18 antibodies. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise anti-IL-12, anti-TNFα, or anti-IL18 antibodies of this disclosure.

Recombinant human antibodies of the invention, including, but not limited to, anti-IL-12, anti-TNFα, or anti-IL-18 antibodies or an antigen binding portion thereof, or anti-IL-12-related, anti-TNFα-related, or anti-IL-18-related antibodies disclosed herein can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the methods of the invention include anti-IL-12, anti-TNFα, or anti-IL-18 antibodies and antibody portions, anti-IL-12-related, anti-TNFα-related, or anti-IL-18-related antibodies and antibody portions, and human antibodies and antibody portions with equivalent properties to anti-IL-12, anti-TNFα, or anti-IL-18 antibodies, such as high affinity binding to hIL-12, hTNFα, or hIL-18 with low dissociation kinetics and high neutralizing capacity. In one aspect, the invention provides treatment with an isolated human antibody, or an antigen-binding portion thereof, that dissociates from hIL-12, hTNFα, or hIL-18 with a Kd of about $1\times10^{-8}$ M or less and a Koff rate constant of $1\times10^{-3}$ s-1 or less, both determined by surface plasmon resonance. In specific non-limiting embodiments, an anti-IL12 antibody purified according to the invention competitively inhibits binding of ABT-874 to IL12 under physiological conditions. In specific non-limiting embodiments, an anti-IL-18 antibody purified according to the invention competitively inhibits binding of ABT-325 to IL-18 under physiological conditions. In specific non-limiting embodiments, an anti-TNFα antibody purified according to the invention competitively inhibits binding of Adalimumab to TNFα under physiological conditions.

In yet another embodiment of the invention, antibodies or fragments thereof, such as but not limited to anti-IL-12, anti-TNFα, or anti-IL-18 antibodies or fragments thereof, can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173: 1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

3. Antibody Production

To express an antibody of the invention, DNAs encoding partial or full-length light and heavy chains are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into a separate vector or, more typically, both genes are inserted into the same expression vector. The antibody genes are inserted into an expression vector by standard methods (e.g., ligation of complementary restriction sites on the antibody gene fragment and vector, or blunt end ligation if no restriction sites are present). Prior to insertion of the antibody or antibody-related light or heavy chain sequences, the expression vector may already carry antibody constant region sequences. For example, one approach to converting the anti-IL-12, anti-TNFα, or anti-IL-18 antibody or anti-IL-12, anti-TNFα, or anti-IL-18 antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, a recombinant expression vector of the invention can carry one or more regulatory sequence that controls the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the antibody chain genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of the light and heavy chains, the expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. lichenifonnis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger.*

Suitable host cells for the expression of glycosylated antibodies are derived from multicellular organisms. Examples of invertebrate cells include plant and insect cells. Numerous baculoviral strains and variants and corresponding permissive insect host cells from hosts such as *Spodoptera fru-* giperda (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant antibodies of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NSO myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/−DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce an antibody may be cultured in a variety of media. Commercially available media such as Ham's F10™ (Sigma), Minimal Essential Medium™ ((MEM), (Sigma), RPMI-1640 (Sigma), and Dulbecco's Modified Eagle's Medium™ ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact antibodies, such as Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to IL-12, specifically hIL-12, in the context of anti-IL-12 antibodies or that DNA not necessary for binding to IL-18, specifically hIL-18, in the context of anti-IL-18 antibodies, or that DNA not necessary for binding to TNFα, specifically hTNFα, in the context of anti-TNFα antibodies. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than IL-12, TNFα, or IL-18, depending on the specificity of the antibody of the invention, by crosslinking an antibody of the invention to a second antibody by standard chemical crosslinking methods.

In a suitable system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

When using recombinant techniques, the antibody can be produced intracellularly, in the periplasmic space, or directly secreted into the medium. In one aspect, if the antibody is produced intracellularly, as a first step, the particulate debris, either host cells or lysed cells (e.g., resulting from homogenization), can be removed, e.g., by centrifugation or ultrafiltration. Where the antibody is secreted into the medium, supernatants from such expression systems can be first concentrated using a commercially available protein concentration filter, e.g., an Amicon™ or Millipore Pellicon™ ultrafiltration unit.

Prior to the process of the invention, procedures for purification of antibodies from cell debris initially depend on the site of expression of the antibody. Some antibodies can be secreted directly from the cell into the surrounding growth media; others are made intracellularly. For the latter antibodies, the first step of a purification process typically involves: lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. Where the antibody is secreted, supernatants from such expression systems are generally first concentrated using a commercially available protein concentration filter, e.g., an Amicon™ or Millipore Pellicon™ ultrafiltration unit. Where the antibody is secreted into the medium, the recombinant host cells can also be separated from the cell culture medium, e.g., by tangential flow filtration. Antibodies can be further recovered from the culture medium using the antibody purification methods of the invention.

4. Antibody Purification 4.1 Antibody Purification Generally

The invention provides a method for producing a purified (or "HCP-reduced") antibody preparation from a mixture comprising an antibody and at least one HCP. The purification process of the invention begins at the separation step when the antibody has been produced using methods described above and conventional methods in the art. Table 1 summarizes one embodiment of a purification scheme. Variations of this scheme, including, but not limited to, variations where the Protein A affinity chromatography step is omitted or the order of the ion exchange steps is reversed, are envisaged and are within the scope of this invention.

TABLE 1

Purification steps with their associated purpose

| Purification step | Purpose |
| --- | --- |
| Primary recovery | clarification of sample matrix |
| Affinity chromatography | antibody capture, host cell protein and associated impurity reduction |
| Cation exchange chromatography | antibody capture, host cell protein and associated impurity reduction |
| ultrafiltration/diafiltration | concentration and buffer exchange |
| Anion exchange chromatography | reduction of host cell proteins and DNA |
| Phenyl Sepharose ™ HP chromatography | reduction of antibody aggregates and host cell proteins |
| Viral filtration | removal of large viruses, if present |
| Final ultrafiltration/diafiltration | concentrate and formulate antibody |

Once a clarified solution or mixture comprising the antibody has been obtained, separation of the antibody from the other proteins produced by the cell, such as HCPs, is performed using a combination of different purification techniques, including ion exchange separation step(s) and hydrophobic interaction separation step(s). The separation steps separate mixtures of proteins on the basis of their charge, degree of hydrophobicity, or size. In one aspect of the invention, separation is performed using chromatography, including cationic, anionic, and hydrophobic interaction. Several different chromatography resins are available for each of these techniques, allowing accurate tailoring of the purification scheme to the particular protein involved. The essence of each of the separation methods is that proteins can be caused either to traverse at different rates down a column, achieving a physical separation that increases as they pass further down the column, or to adhere selectively to the separation medium, being then differentially eluted by different solvents. In some cases, the antibody is separated from impurities when the impurities specifically adhere to the column and the antibody does not, i.e., the antibody is present in the flow through.

As noted above, accurate tailoring of a purification scheme relies on consideration of the protein to be purified. In certain embodiments, the separation steps of the instant invention are employed to separate an antibody from one or more HCPs. Antibodies that can be successfully purified using the methods described herein include, but are not limited to, human $IgA_1$, $IgA_2$, IgD, IgE, $IgG_1$, $IgG_2$, $IgG_3$, $IgG_4$, and IgM antibodies. In certain embodiments, the purification strategies of the instant invention exclude the use of Protein A affinity chromatography, for example in the context of the purification of $IgG_3$ antibodies, as $IgG_3$ antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

4.2 Primary Recovery

The initial steps of the purification methods of the present invention involve the first phase of clarification and primary recovery of antibody from a sample matrix. In addition, the primary recovery process can also be a point at which to reduce or inactivate viruses that can be present in the sample matrix. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire teaching of which is incorporated herein by reference. In certain embodiments of the present invention, the sample matrix is exposed to pH viral reduction/inactivation during the primary recovery phase.

Methods of pH viral reduction/inactivation include, but are not limited to, incubating the mixture for a period of time at low pH, and subsequently neutralizing the pH and removing particulates by filtration. In certain embodiments the mixture will be incubated at a pH of between about 2 and 5, preferably at a pH of between about 3 and 4, and more preferably at a pH of about 3.5. The pH of the sample mixture may be lowered by any suitable acid including, but not limited to, citric acid, acetic acid, caprylic acid, or other suitable acids. The choice of pH level largely depends on the stability profile of the antibody product and buffer components. It is known that the quality of the target antibody during low pH virus reduction/inactivation is affected by pH and the duration of the low pH incubation. In certain embodiments the duration of the low pH incubation will be from 0.5 hr to two 2 hr, preferably 0.5 hr to 1.5 hr, and more preferably the duration will be 1 hr. Virus reduction/inactivation is dependent on these same parameters in addition to protein concentration, which may limit reduction/inactivation at high concentrations. Thus, the proper parameters of protein concentration, pH, and duration of reduction/inactivation can be selected to achieve the desired level of viral reduction/inactivation.

In certain embodiments viral reduction/inactivation can be achieved via the use of suitable filters. A non-limiting example of a suitable filter is the Ultipor DV50™ filter from Pall Corporation. Although certain embodiments of the present invention employ such filtration during the primary recovery phase, in other embodiments it is employed at other phases of the purification process, including as either the penultimate or final step of purification. In certain embodiments, alternative filters are employed for viral reduction/inactivation, such as, but not limited to, Viresolve™ filters (Millipore, Billerica, Mass.); Zeta Plus VR™ filters (CUNO; Meriden, Conn.); and Planova™ filters (Asahi Kasei Pharma, Planova Division, Buffalo Grove, Ill.).

In those embodiments where viral reduction/inactivation is employed, the sample mixture can be adjusted, as needed, for further purification steps. For example, following low pH viral reduction/inactivation the pH of the sample mixture is typically adjusted to a more neutral pH, e.g., from about 4.5 to about 8.5, and preferably about 4.9, prior to continuing the purification process. Additionally, the mixture may be flushed with water for injection (WFI) to obtain a desired conductivity.

In certain embodiments, the primary recovery will include one or more centrifugation steps to further clarify the sample matrix and thereby aid in purifying the anti-IL-12, anti-TNFα, or anti-IL-18 antibodies. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery will include the use of one or more depth filtration steps to further clarify the sample matrix and thereby aid in purifying the antibodies of the present invention. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments the depth filtration step can be a delipid depth filtration step. Although certain embodiments employ depth filtration steps only during the primary recovery phase, other embodiments employ depth filters, including delipid depth filters, during one or more additional phases of purification. Non-limiting examples of depth filters that can be used in the context of the instant invention include the Cuno™ model 30/60ZA depth filters (3M Corp.), and 0.45/0.2 µm Sartopore™ bi-layer filter cartridges.

4.3 Affinity Chromatography

In certain embodiments, the primary recovery sample is subjected to affinity chromatography to further purify the antibody of interest away from HCPs. In certain embodiments the chromatographic material is capable of selectively or specifically binding to the antibody of interest. Non-limiting examples of such chromatographic material include: Protein A, Protein G, chromatographic material comprising the antigen bound by the antibody of interest, and chromatographic material comprising an Fc binding protein. In specific embodiments, the affinity chromatography step involves subjecting the primary recovery sample to a column comprising a suitable Protein A resin. Protein A resin is useful for affinity purification and isolation of a variety antibody isotypes, particularly $IgG_1$, $IgG_2$, and $IgG_4$. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin is MabSelect™ from GE Healthcare. A non-limiting example of a suitable column packed with Mab-Select™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™

In certain embodiments it will be advantageous to identify the dynamic binding capacity (DBC) of the Protein A resin in order to tailor the purification to the particular antibody of interest. For example, but not by way of limitation, the DBC of a MabSelect™ column can be determined either by a single flow rate load or dual-flow load strategy. The single flow rate load can be evaluated at a velocity of about 300 cm/hr throughout the entire loading period. The dual-flow rate load strategy can be determined by loading the column up to about 35 mg protein/mL resin at a linear velocity of about 300 cm/hr, then reducing the linear velocity by half to allow longer residence time for the last portion of the load.

In certain embodiments, the Protein A column can be equilibrated with a suitable buffer prior to sample loading. A non-limiting example of a suitable buffer is a Tris/NaCl buffer, pH of about 7.2. A non-limiting example of suitable equilibration conditions is 25 mM Tris, 100 mM NaCl, pH of about 7.2. Following this equilibration, the sample can be loaded onto the column. Following the loading of the column, the column can be washed one or multiple times using, e.g., the equilibrating buffer. Other washes, including washes employing different buffers, can be employed prior to eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. A non-limiting example of a suitable elution buffer is an acetic acid/NaCl buffer, pH of about 3.5. Suitable conditions are, e.g., 0.1 M acetic acid, pH of about 3.5. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

4.4 Ion Exchange Chromatography

In certain embodiments, the instant invention provides methods for producing a HCP-reduced antibody preparation from a mixture comprising an antibody and at least one HCP by subjecting the mixture to at least one ion exchange separation step such that an eluate comprising the antibody is obtained. Ion exchange separation includes any method by which two substances are separated based on the difference in their respective ionic charges, and can employ either cationic exchange material or anionic exchange material.

The use of a cationic exchange material versus an anionic exchange material is based on the overall charge of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial antibody mixture can be contacted with the ion exchange material by using any of a variety of techniques, e.g., using a batch purification technique or a chromatographic technique.

For example, in the context of batch purification, ion exchange material is prepared in, or equilibrated to, the desired starting buffer. Upon preparation, or equilibration, a slurry of the ion exchange material is obtained. The antibody solution is contacted with the slurry to adsorb the antibody to be separated to the ion exchange material. The solution comprising the HCP(s) that do not bind to the ion exchange material is separated from the slurry, e.g., by allowing the slurry to settle and removing the supernatant. The slurry can be subjected to one or more wash steps. If desired, the slurry can be contacted with a solution of higher conductivity to desorb HCPs that have bound to the ion exchange material. In order to elute bound polypeptides, the salt concentration of the buffer can be increased.

Ion exchange chromatography may also be used as an ion exchange separation technique. Ion exchange chromatography separates molecules based on differences between the overall charge of the molecules. For the purification of an antibody, the antibody must have a charge opposite to that of the functional group attached to the ion exchange material, e.g., resin, in order to bind. For example, antibodies, which generally have an overall positive charge in the buffer pH below its pI, will bind well to cation exchange material, which contain negatively charged functional groups.

In ion exchange chromatography, charged patches on the surface of the solute are attracted by opposite charges attached to a chromatography matrix, provided the ionic strength of the surrounding buffer is low. Elution is generally achieved by increasing the ionic strength (i.e., conductivity) of the buffer to compete with the solute for the charged sites of the ion exchange matrix. Changing the pH and thereby altering the charge of the solute is another way to achieve elution of the solute. The change in conductivity or pH may be gradual (gradient elution) or stepwise (step elution).

Anionic or cationic substituents may be attached to matrices in order to form anionic or cationic supports for chromatography. Non-limiting examples of anionic exchange substituents include diethylaminoethyl (DEAE), quaternary aminoethyl(QAE) and quaternary amine(Q) groups. Cationic substitutents include carboxymethyl (CM), sulfoethyl(SE), sulfopropyl(SP), phosphate(P) and sulfonate(S). Cellulose ion exchange resins such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa.

A mixture comprising an antibody and impurities, e.g., HCP(s), is loaded onto an ion exchange column, such as a cation exchange column. For example, but not by way of limitation, the mixture can be loaded at a load of about 80 g protein/L resin depending upon the column used. An example of a suitable cation exchange column is a 80 cm diameter×23 cm long column whose bed volume is about 116 L. The mixture loaded onto this cation column can subsequently washed with wash buffer (equilibration buffer). The antibody is then eluted from the column, and a first eluate is obtained.

This ion exchange step facilitates the capture of the antibody of interest while reducing impurities such as HCPs. In certain aspects, the ion exchange column is a cation exchange column. For example, but not by way of limitation, a suitable resin for such a cation exchange column is CM HyperDF resin. These resins are available from commercial sources such as Pall Corporation. This cation exchange procedure can be carried out at or around room temperature.

4.5 Ultrafiltration/Diafiltration

Certain embodiments of the present invention employ ultrafiltration and/or diafiltration steps to further purify and concentrate the antibody sample. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 µm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained antibody. In certain embodiments of the present invention, a diafiltration step is employed to exchange the various buffers used in connection with the instant invention, optionally prior to further chromatography or other purification steps, as well as to remove impurities from the antibody preparations.

4.6 Hydrophobic Interaction Chromatography

The present invention also features methods for producing a HCP-reduced antibody preparation from a mixture comprising an antibody and at least one HCP further comprising a hydrophobic interaction separation step. For example, a first eluate obtained from an ion exchange column can be subjected to a hydrophobic interaction material such that a second eluate having a reduced level of HCP is obtained. Hydrophobic interaction chromatography steps, such as those disclosed herein, are generally performed to remove protein aggregates, such as antibody aggregates, and process-related impurities.

In performing the separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

For example, in the context of batch purification, HIC material is prepared in or equilibrated to the desired equilibration buffer. A slurry of the HIC material is obtained. The antibody solution is contacted with the slurry to adsorb the antibody to be separated to the HIC material. The solution comprising the HCPs that do not bind to the HIC material is separated from the slurry, e.g., by allowing the slurry to settle and removing the supernatant. The slurry can be subjected to one or more washing steps. If desired, the slurry can be contacted with a solution of lower conductivity to desorb antibodies that have bound to the HIC material. In order to elute bound antibodies, the salt concentration can be decreased.

Whereas ion exchange chromatography relies on the charges of the antibodies to isolate them, hydrophobic interaction chromatography uses the hydrophobic properties of the antibodies. Hydrophobic groups on the antibody interact with hydrophobic groups on the column. The more hydrophobic a protein is the stronger it will interact with the column. Thus the HIC step removes host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the antibody to a HIC column is favored by high salt concentrations, but the actual concentrations can vary over a wide range depending on the nature of the antibody and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as Ba++; Ca++; Mg++; Li+; Cs+; Na+; K+; Rb+; NH4+, while anions may be ranked in terms of increasing chaotropic effect as PO---; SO4--; CH3CO3-; Cl-; Br-; NO3-; ClO4-; I-; SCN-.

In general, Na, K or NH4 sulfates effectively promote ligand-protein interaction in HIC. Salts may be formulated that influence the strength of the interaction as given by the following relationship: (NH4)2SO4>Na2SO4>NaCl>NH4Cl>NaBr>NaSCN. In general, salt concentrations of between about 0.75 and about 2 M ammonium sulfate or between about 1 and 4 M NaCl are useful.

HIC columns normally comprise a base matrix (e.g., cross-linked agarose or synthetic copolymer material) to which hydrobobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Methyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, Pa.)

4.7 Exemplary Purification Strategies

In certain embodiments, primary recovery can proceed by sequentially employing pH reduction, centrifugation, and filtration steps to remove cells and cell debris (including HCPs) from the production bioreactor harvest. For example, but not by way of limitation, a culture comprising antibodies, media, and cells can be subjected to pH-mediated virus reduction/inactivation using an acid pH of about 3.5 for approximately 1 hour. The pH reduction can be facilitated using known acid preparations such as citric acid, e.g., 3 M citric acid. Exposure to acid pH reduces, if not completely eliminates, pH sensitive viral contaminants and precipitates some media/cell contaminants. Following this viral reduction/inactivation step, the pH is adjusted to about 4.9 or 5.0 using a base such as sodium hydroxide, e.g., 3 M sodium hydroxide, for about twenty to about forty minutes. This adjustment can occur at around 20° C. In certain embodiments, the pH adjusted culture then centrifuged at approximately 7000×g to approximately 11,000× g. In certain embodiments, the resulting sample supernatant is then passed through a filter train comprising multiple depth filters. In certain embodiments, the filter train comprises around twelve 16-inch Cuno™ model 30/60ZA depth filters (3M Corp.) and around three round filter housings fitted with three 30-inch 0.45/0.2 µm Sartopore™ 2 filter cartridges (Sartorius). The clarified supernatant is collected in a vessel such as a pre-sterilized harvest vessel and held at approximately 8° C. This temperature is then adjusted to approximately 20° C. prior to the capture chromatography step or steps outlined below. It should be noted that one skilled in the art may vary the conditions recited above and still be within the scope of the present invention.

In certain embodiments, primary recovery will be followed by affinity chromatography using Protein A resin. There are several commercial sources for Protein A resin. One suitable resin is MabSelect™ from GE Healthcare. An example of a suitable column packed with MabSelect™ is a column about 1.0 cm diameter×about 21.6 cm long (~17 mL bed volume). This size column can be used for bench scale. This can be compared with other columns used for scale ups. For example, a 20 cm×21 cm column whose bed volume is about 6.6 L can be used for commercial production. Regardless of the column, the column can be packed using a suitable resin such as MabSelect™

In certain aspects, the Protein A column can be equilibrated with a suitable buffer prior to sample loading. An example of a suitable buffer is a Tris/NaCl buffer, pH of about 6 to 8, preferably about 7.2. A specific example of suitable conditions is 25 mM Tris, 100 mM NaCl, pH 7.2. Following this equilibration, the sample can be loaded onto the column. Following the loading of the column, the column can be washed one or multiple times using, e.g., the equilibrating buffer. Other washes including washes employing different buffers can be used before eluting the column. For example, the column can be washed using one or more column volumes of 20 mM citric acid/sodium citrate, 0.5 M NaCl at pH of about 6.0. This wash can optionally be followed by one or more washes using the equilibrating buffer. The Protein A column can then be eluted using an appropriate elution buffer. An example of a suitable elution buffer is an acetic acid/NaCl buffer, pH around 3.5. Suitable conditions are, e.g., 0.1 M acetic acid, pH 3.5. The eluate can be monitored using techniques well known to those skilled in the art. For example, the absorbance at $OD_{280}$ can be followed. Column eluate can be collected starting with an initial deflection of about 0.5 AU to a reading of about 0.5 AU at the trailing edge of the elution peak. The elution fraction(s) of interest can then be prepared for further processing. For example, the collected sample can be titrated to a pH of about 5.0 using Tris (e.g., 1.0 M) at a pH of about 10. Optionally, this titrated sample can be filtered and further processed.

The dynamic binding capacity (DBC) of the MabSelect™ column can be determined either by a single flow rate load or dual-flow load strategy. The single flow rate load can be evaluated at a velocity of about 300 cm/hr throughout the entire loading period. The dual-flow rate load strategy can be determined by loading the column up to about 35 mg protein/mL resin at a linear velocity of about 300 cm/hr, then reducing the linear velocity by half to allow longer residence time for the last portion of the load.

The Protein A eluate can then be further purified using a cation exchange column. In certain embodiments, the equilibrating buffer used in the cation exchange column is a buffer having a pH of about 5.0. An example of a suitable buffer is about 210 mM sodium acetate, pH 5.0. Following equilibration, the column is loaded with sample prepared from the primary recovery step above. The column is packed with a cation exchange resin, such as CM Sepharose™ Fast Flow from GE Healthcare. The column is then washed using the equilibrating buffer. The column is next subjected to an elution step using a buffer having a greater ionic strength as compared to the equilibrating or wash buffer. For example, a suitable elution buffer can be about 790 mM sodium acetate, pH 5.0. The antibodies will be eluted and can be monitored using a UV spectrophotometer set at $OD_{280nm}$. In a particular example, elution collection can be from upside 3 $OD_{280nm}$ to downside 8 $OD_{280nm}$. It should be understood that one skilled in the art may vary the conditions and yet still be within the scope of the invention.

In certain embodiments the Protein A eluate is instead further purified using an anion exchange column. A non-limiting example of a suitable column for this step is a 60 cm diameter×30 cm long column whose bed volume is about 85 L. The column is packed with an anion exchange resin, such as Q Sepharose™ Fast Flow from GE Healthcare. The column can be equilibrated using about seven column volumes of an appropriate buffer such as Tris/sodium chloride. An example of suitable conditions are 25 mM Tris, 50 mM sodium chloride at pH 8.0. A skilled artisan may vary the conditions but still be within the scope of the present invention. The column is loaded with the collected sample from the Protein A purification step outlined above. In another aspect, the column is loaded from the eluate collected during cation exchange. Following the loading of the column, the column is washed with the equilibration buffer (e.g., the Tris/sodium chloride buffer). The flow-through comprising the antibodies can be monitored using a UV spectrophotometer at $OD_{280nm}$. This anion exchange step reduces process related impurities such as nucleic acids like DNA, and host cell proteins. The separation occurs due to the fact that the antibodies of interest do not substantially interact with nor bind to the solid phase of the column, e.g., to the Q Sepharose™, but many impurities do interact with and bind to the column's solid phase. The anion exchange can be performed at about 12° C.

In certain embodiments, the cation exchange or anion exchange eluate, depending on which ion exchange step is employed first, is next filtered using, e.g., a 16 inch Cuno™ delipid filter. This filtration, using the delipid filter, can be followed by, e.g., a 30-inch 0.45/0.2 µm Sartopore™ bi-layer filter cartridge. The ion exchange elution buffer can be used to flush the residual volume remaining in the filters and prepared for ultrafiltration/diafiltration.

In order to accomplish the ultratfiltration/diafiltration step, the filtration media is prepared in a suitable buffer, e.g., 20 mM sodium phosphate, pH 7.0. A salt such as sodium chloride can be added to increase the ionic strength, e.g., 100 mM sodium chloride. This ultrafiltration/diafiltration step serves to concentrate the anti-IL-12, anti-TNFα, or anti-IL-18 antibodies, remove the sodium acetate and adjust the pH. Commercial filters are available to effectuate this step. For example, Millipore manufactures a 30 kD molecular weight cut-off (MWCO) cellulose ultrafilter membrane cassette. This filtration procedure can be conducted at or around room temperature.

In certain embodiments, the sample from the capture filtration step above is subjected to a second ion exchange separation step. Preferably this second ion exchange separation will involve separation based on the opposite charge of the first ion exchange separation. For example, if an anion exchange step is employed after primary recovery, the second ion exchange chromatographic step may be a cation exchange step. Conversely, if the primary recovery step was followed by a cation exchange step, that step would be followed by an anion exchange step. In certain embodiments the first ion exchange eluate can be subjected directly to the second ion exchange chromatographic step where the first ion exchange eluate is adjusted to the appropriate buffer conditions. Suitable anionic and cationic separation materials and conditions are described above.

In certain embodiments of the instant invention the sample containing antibodies will be further processed using a hydrophobic interaction separation step. A non-limiting example of a suitable column for such a step is an 80 cm diameter×15 cm long column whose bed volume is about 75 L, which is packed with an appropriate resin used for HIC such as, but not limited to, Phenyl HP Sepharose™ from Amersham Biosciences, Upsala, Sweden. The flow-through preparation obtained from the previous anion exchange chromatography step comprising the antibodies of interest can be diluted with an equal volume of around 1.7 M ammonium sulfate, 50 mM sodium phosphate, pH 7.0. This then can be subjected to filtration using a 0.45/0.2 µm Sartopore™ 2 bi-layer filter, or its equivalent. In certain embodiments, the hydrophobic chromatography procedure involves two or more cycles.

In certain embodiments, the HIC column is first equilibrated using a suitable buffer. A non-limiting example of a suitable buffer is 0.85 M ammonium sulfate, 50 mM sodium phosphate, pH 7.0. One skilled in the art can vary the equilibrating buffer and still be within the scope of the present invention by altering the concentrations of the buffering agents and/or by substituting equivalent buffers. In certain embodiments the column is then loaded with an anion exchange flow-through sample and washed multiple times, e.g., three times, with an appropriate buffer system such as ammonium sulfate/sodium phosphate. An example of a suitable buffer system includes 1.1 M ammonium sulfate, 50 mM sodium phosphate buffer with a pH of around 7.0. Optionally, the column can undergo further wash cycles. For example, a second wash cycle can include multiple column washes, e.g., one to seven times, using an appropriate buffer system. A non-limiting example of a suitable buffer system includes 0.85 M ammonium sulfate, 50 mM sodium phosphate, pH 7.0. In one aspect, the loaded column undergoes yet a third wash using an appropriate buffer system. The column can be washed multiple times, e.g., one to three times, using a buffer system such as 1.1 M ammonium sulfate, 50 mM sodium phosphate at a pH around 7.0. Again, one skilled in the art can vary the buffering conditions and still be within the scope of the present invention.

The column is eluted using an appropriate elution buffer. A suitable example of such an elution buffer is 0.5 M ammonium sulfate, 15 mM sodium phosphate at a pH around 7.0. The antibodies of interest can be detected and collected using a conventional spectrophotometer from the upside at 3 $OD_{280\ nm}$ to downside of peak at 3 $OD_{280\ nm}$.

In certain aspects of the invention, the eluate from the hydrophobic chromatography step is subjected to filtration for the removal of viral particles, including intact viruses, if present. A non-limiting example of a suitable filter is the Ultipor DV50™ filter from Pall Corporation. Other viral filters can be used in this filtration step and are well known to those skilled in the art. The HIC eluate is passed through a pre-wetted filter of about 0.1 µm and a 2×30-inch Ultipor DV50™ filter train at around 34 psig. In certain embodiments, following the filtration process, the filter is washed using, e.g., the HIC elution buffer in order to remove any antibodies retained in the filter housing. The filtrate can be stored in a pre-sterilized container at around 12° C.

In a certain embodiments, the filtrate from the above is again subjected to ultrafiltration/diafiltration. This step is important if a practitioner's end point is to use the antibody in a, e.g., pharmaceutical formulation. This process, if employed, can facilitate the concentration of antibody, removal of buffering salts previously used and replace it with a particular formulation buffer. In certain embodiments, continuous diafiltration with multiple volumes, e.g., two volumes, of a formulation buffer is performed. A non-limiting example of a suitable formulation buffer is 5 mM methionine, 2% mannitol, 0.5% sucrose, pH 5.9 buffer (no Tween). Upon completion of this diavolume exchange the antibodies are concentrated. Once a predetermined concentration of antibody has been achieved, then a practitioner can calculate the amount of 10% Tween that should be added to arrive at a final Tween concentration of about 0.005% (v/v).

Certain embodiments of the present invention will include further purification steps. Examples of additional purification procedures which can be performed prior to, during, or following the ion exchange chromatography method include ethanol precipitation, isoelectric focusing, reverse phase HPLC, chromatography on silica, chromatography on heparin Sepharose™, further anion exchange chromatography and/or further cation exchange chromatography, chromatofocusing, SDS-PAGE, ammonium sulfate precipitation, hydroxylapatite chromatography, gel electrophoresis, dialysis, and affinity chromatography (e.g., using protein G, an antibody, a specific substrate, ligand or antigen as the capture reagent).

In certain embodiments of the present invention, the anti-IL-12 antibody is an $IgA_1$, $IgA_2$, IgD, IgE, $IgG_1$, $IgG_2$, $IgG_3$, $IgG_4$, or IgM isotype antibody comprising the heavy and light chain variable region sequences outlined in FIG. 1. In preferred embodiments, the anti-IL-12 antibody is an $IgG_1$, $IgG_2$, $IgG_3$ or $IgG_4$ isotype antibody comprising the heavy and light chain variable region sequences outlined in FIG. 1, more preferably the anti-IL-12 antibody is an $IgG_1$ antibody comprising the heavy and light chain variable region sequences outlined in FIG. 1. In certain embodiments of the present invention, the anti-TNFα antibody is an $IgA_1$, $IgA_2$, IgD, IgE, $IgG_1$, $IgG_2$, $IgG_3$, $IgG_4$, or IgM isotype antibody comprising the heavy and light chain variable region sequences outlined in FIG. 3. In preferred embodiments, the anti-TNFα antibody is an $IgG_1$, $IgG_2$, $IgG_3$ or $IgG_4$ isotype antibody comprising the heavy and light chain variable region sequences outlined in FIG. 3, more preferably the anti-TNFα antibody is an $IgG_1$ antibody comprising the heavy and light chain variable region sequences outlined in FIG. 3.

5. Methods of Assaying Sample Purity

5.1 Assaying Host Cell Protein

The present invention also provides methods for determining the residual levels of host cell protein (HCP) concentration in the isolated/purified antibody composition. As described above, HCPs are desirably excluded from the final target substance product, e.g., the anti-IL-12, anti-TNFα, or anti-IL-18 antibody. Exemplary HCPs include proteins originating from the source of the antibody production. Failure to identify and sufficiently remove HCPs from the target antibody may lead to reduced efficacy and/or adverse subject reactions.

As used herein, the term "HCP ELISA" refers to an ELISA where the second antibody used in the assay is specific to the HCPs produced from cells, e.g., CHO cells, used to generate the antibody (e.g., anti-IL-12, anti-TNFα, or anti-IL-18 antibody). The second antibody may be produced according to conventional methods known to those of skill in the art. For example, the second antibody may be produced using HCPs obtained by sham production and purification runs, i.e., the same cell line used to produce the antibody of interest is used, but the cell line is not transfected with antibody DNA. In an exemplary embodiment, the second antibody is produced using HPCs similar to those expressed in the cell expression system of choice, i.e., the cell expression system used to produce the target antibody.

Generally, HCP ELISA comprises sandwiching a liquid sample comprising HCPs between two layers of antibodies, i.e., a first antibody and a second antibody. The sample is incubated during which time the HCPs in the sample are captured by the first antibody, for example, but not limited to goat anti-CHO, affinity purified (Cygnus). A labeled second antibody, or blend of antibodies, specific to the HCPs produced from the cells used to generate the antibody, e.g., anti-CHO HCP Biotinylated, is added, and binds to the HCPs within the sample. In certain embodiments the first and second antibodies are polyclonal antibodies. In certain aspects the first and second antibodies are blends of polyclonal antibodies raised against HCPs, for example, but not limited to Biotinylated goat anti Host Cell Protein Mixture 599/626/748. The amount of HCP contained in the sample is determined using the appropriate test based on the label of the second antibody.

HCP ELISA may be used for determining the level of HCPs in an antibody composition, such as an eluate or flow-through obtained using the process described above. The present invention also provides a composition comprising an antibody, wherein the composition has no detectable level of HCPs as determined by an HCP Enzyme Linked Immunosorbent Assay ("ELISA").

5.2 Assaying Affinity Chromatographic Material

In certain embodiments, the present invention also provides methods for determining the residual levels of affinity chromatographic material in the isolated/purified antibody composition. In certain contexts such material leaches into the antibody composition during the purification process. In certain embodiments, an assay for identifying the concentration of Protein A in the isolated/purified antibody composition is employed. As used herein, the term "Protein A ELISA" refers to an ELISA where the second antibody used in the assay is specific to the Protein A employed to purify the antibody of interest, e.g., an anti-IL-12, anti-TNFα, or anti-IL-18 antibody. The second antibody may be produced according to conventional methods known to those of skill in the art. For example, the second antibody may be produced using naturally occurring or recombinant Protein A in the context of conventional methods for antibody generation and production.

Generally, Protein A ELISA comprises sandwiching a liquid sample comprising Protein A (or possibly containing Protein A) between two layers of anti-Protein A antibodies, i.e., a first anti-Protein A antibody and a second anti-Protein A antibody. The sample is exposed to a first layer of anti-Protein A antibody, for example, but not limited to polyclonal antibodies or blends of polyclonal antibodies, and incubated for a time sufficient for Protein A in the sample to be captured by the first antibody. A labeled second antibody, for example, but not limited to polyclonal antibodies or blends of polyclonal antibodies, specific to the Protein A is then added, and binds to the captured Protein A within the sample. Additional non-limiting examples of anti-Protein A antibodies useful in the context of the instant invention include chicken anti-Protein A and biotinylated anti-Protein A antibodies. The amount of Protein A contained in the sample is determined using the appropriate test based on the label of the second antibody.

Similar assays can be employed to identify the concentration of alternative affinity chromatographic materials.

Protein A ELISA may be used for determining the level of Protein A in an antibody composition, such as an eluate or flow-through obtained using the process described in above. The present invention also provides a composition comprising an antibody, wherein the composition has no detectable level of Protein A as determined by an Protein A Enzyme Linked Immunosorbent Assay ("ELISA").

6. Further Modifications

The antibodies of the present invention can be modified. In some embodiments, the antibodies or antigen binding fragments thereof are chemically modified to provide a desired effect. For example, pegylation of antibodies or antibody fragments of the invention may be carried out by any of the pegylation reactions known in the art, as described, e.g., in the following references: Focus on Growth Factors 3:4-10 (1992); EP 0 154 316; and EP 0 401 384, each of which is incorporated by reference herein in its entirety. In one aspect, the pegylation is carried out via an acylation reaction or an alkylation reaction with a reactive polyethylene glycol molecule (or an analogous reactive water-soluble polymer). A suitable water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (C1—C10) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under suitable conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments specific for IL-12, TNFα, or IL-18 may generally be used to treat IL-12-related, TNFα-related, or IL-18-related disorders of the invention by administration of the anti-IL-12, anti-TNFα or anti-IL-18 antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

An antibody or antibody portion of the invention can be derivatized or linked to another functional molecule (e.g., another peptide or protein). Accordingly, the antibodies and antibody portions of the invention are intended to include derivatized and otherwise modified forms of the human anti-hIL-12, anti-TNFα, or anti-hIL-18 antibodies described herein, including immunoadhesion molecules. For example, an antibody or antibody portion of the invention can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

One type of derivatized antibody is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

7. Pharmaceutical Compositions

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The antibodies and antibody-portions of the invention can be incorporated into a pharmaceutical composition suitable for parenteral administration. The antibody or antibody-portions can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80

(optimally 0.005-0.01%). Additional surfactants include but are not limited to polysorbate 20 and BRIJ surfactants.

In one aspect, the pharmaceutical composition includes the antibody at a dosage of about 0.01 mg/kg-10 mg/kg. In another aspect, the dosages of the antibody include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the antibody is administered by intravenous infusion or injection. In another aspect, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The antibodies and antibody-portions of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, an antibody or antibody portion of the invention may be orally administered, e.g., with an inert diluent or an assailable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, an antibody or antibody portion of the invention is co-formulated with and/or co-administered with one or more additional therapeutic agents that are useful for treating disorders in which IL-12, TNFα, or IL-18 activity is detrimental. For example, an anti-hIL-12, anti-TNFα or anti-IL-18 antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the antibodies of the invention are used as part of a combination therapy, a lower dosage of antibody may be desirable than when the antibody alone is administered to a subject (e.g., a synergistic therapeutic effect may be achieved through the use of combination therapy which, in turn, permits use of a lower dose of the antibody to achieve the desired therapeutic effect).

It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent which imparts a beneficial attribute to the therapeutic composition, e.g., an agent which effects the viscosity of the composition.

It should further be understood that the combinations which are to be included within this invention are those combinations useful for their intended purpose. The agents set forth below are illustrative and not intended to be limited. The combinations which are part of this invention can be the antibodies of the present invention and at least one additional agent selected from the lists below. The combination can also include more than one additional agent, e.g., two or three additional agents if the combination is such that the formed composition can perform its intended function.

Some combinations are non-steroidal anti-inflammatory drug(s) also referred to as NSAIDS which include drugs like ibuprofen. Other combinations are corticosteroids including prednisolone; the well known side-effects of steroid use can be reduced or even eliminated by tapering the steroid dose required when treating patients in combination with the antibodies of this invention. Non-limiting examples of therapeutic agents for rheumatoid arthritis with which an antibody, or antibody portion, of the invention can be combined to include the following: cytokine suppressive anti-inflammatory drug(s) (CSAIDs); antibodies to or antagonists of other human cytokines or growth factors, for example, TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, or their ligands including CD 154 (gp39 or CD40L).

Some combinations of therapeutic agents may interfere at different points in the autoimmune and subsequent inflammatory cascade; examples include TNF antagonists like chimeric, humanized or human TNF antibodies, D2E7, (U.S. application Ser. No. 08/599,226 filed Feb. 9, 1996, the entire teaching of which is incorporated herein by reference), cA2 (Remicade™), CDP 571, anti-TNF antibody fragments (e.g., CDP870), and soluble p55 or p75 TNF receptors, derivatives thereof, (p75TNFRIgG (Enbrel™) or p55TNFR1gG (Lenercept), soluble IL-13 receptor (sIL-13), and also TNFα converting enzyme (TACE) inhibitors; similarly IL-1 inhibitors (e.g., Interleukin-1-converting enzyme inhibitors, such as Vx740, or IL-1RA, etc.) may be effective for the same reason. Other combinations include Interleukin 11, anti-P7s and p-selectin glycoprotein ligand (PSGL). Yet other combinations involve other key players of the autoimmune response which may act parallel to, dependent on or in concert with IL-12 function; especially included are IL-18 antagonists including IL-18 antibodies or soluble IL-18 receptors, or IL-18 binding proteins. It has been shown that IL-12 and IL-18 have overlapping but distinct functions and a combination of antagonists to both may be most effective. Yet another combination includes non-depleting anti-CD4 inhibitors. Yet other combinations include antagonists of the co-stimulatory pathway CD80 (B7.1) or CD86 (B7.2) including antibodies, soluble receptors or antagonistic ligands.

The antibodies of the invention, or antigen binding portions thereof, may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), β-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g., IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™) and p55TNFRIgG (Lenercept), sIL-1 RI, sIL-1 RII, sIL-6R, soluble IL-13 receptor (sIL-13)) and anti-inflammatory cytokines (e.g., IL-4, IL-10, IL-11, IL-13 and TGFβ). Some combinations include methotrexate or leflunomide and in moderate or severe rheumatoid arthritis cases, cyclosporine.

Non-limiting examples of therapeutic agents for inflammatory bowel disease with which an antibody, or antibody portion, of the invention can be combined include the following: budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1α monoclonal antibodies, anti-IL-6 monoclonal antibodies, growth factors, elastase inhibitors, pyridinyl-imidazole compounds, antibodies to or antagonists of other human cytokines or growth factors, e.g., TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD90 or their ligands. The antibodies of the invention, or antigen binding portions thereof, may also be combined with agents, such as methotrexate, cyclosporin, FK506, rapamycin, mycophenolate mofetil, leflunomide, NSAIDs, e.g., ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors (e.g., Vx740), anti-P7s, p-selectin glycoprotein ligand (PSGL), TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1 RI, sIL-1 RII, sIL-6R, soluble IL-13 receptor (sIL-13)) and anti-inflammatory cytokines (e.g., IL-4, IL-10, IL-11, IL-13 and TGFβ).

Examples of therapeutic agents for Crohn's disease in which an antibody or an antigen binding portion can be combined include the following: TNF antagonists, e.g., anti-TNF antibodies, D2E7 (U.S. application Ser. No. 08/599,226, filed Feb. 9, 1996, the entire teaching of which is incorporated herein by reference), cA2 (Remicade™), CDP 571, anti-TNF antibody fragments (e.g., CDP870), TNFR-Ig constructs (p75TNFRIgG (Enbrel™) and p55TNFRIgG (Lenercept)), anti-P7s, p-selectin glycoprotein ligand (PSGL), soluble IL-13 receptor (sIL-13), and PDE4 inhibitors. Antibodies of the invention or antigen binding portions thereof, can be combined with corticosteroids, e.g., budenoside and dexamethasone. Antibodies of the invention or antigen binding portions thereof, may also be combined with agents such as sulfasalazine, 5-aminosalicylic acid and olsalazine, and agents which interfere with synthesis or action of proinflammatory cytokines such as IL-1, e.g., IL-1 converting enzyme inhibitors (e.g., Vx740) and IL-1ra. Antibodies of the invention or antigen binding portion thereof may also be used with T cell signaling inhibitors, e.g., tyrosine kinase inhibitors 6-mercaptopurines. Antibodies of the invention or antigen binding portions thereof, can be combined with IL-11.

Non-limiting examples of therapeutic agents for multiple sclerosis with which an antibody, or antibody portion, of the invention can be combined include the following: corticosteroids, prednisolone, methylprednisolone, azathioprine, cyclophosphamide, cyclosporine, methotrexate, 4-aminopyridine, tizanidine, IFNβ1a (Avonex; Biogen), IFNβ1b (Betaseron; Chiron/Berlex), Copolymer 1 (Cop-1, Copaxone, Teva Pharmaceutical Industries, Inc.), hyperbaric oxygen, intravenous immunoglobulin, clabribine, antibodies to or antagonists of other human cytokines or growth factors, e.g., TNF, LT, IL-1, IL-2, IL-6, IL-7, IL-8, IL-15, IL-16, IL-18, EMAP-II, GM-CSF, FGF, and PDGF. Antibodies of the invention, or antigen binding portions thereof, can be combined with antibodies to cell surface molecules such as CD2, CD3, CD4, CD8, CD25, CD28, CD30, CD40, CD45, CD69, CD80, CD86, CD90 or their ligands. The antibodies of the invention, or antigen binding portions thereof, may also be combined with agents, such as methotrexate, cyclosporine, FK506, rapamycin, mycophenolate mofetil, leflunomide, NSAIDs, e.g., ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors (e.g., Vx740), anti-P7s, p-selectin glycoprotein ligand (PSGL), TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1 RI, sIL-1 RII, sIL-6R, soluble IL-13 receptor (sIL-13)) and anti-inflammatory cytokines (e.g., IL-4, IL-10, IL-13 and TGFβ).

Examples of therapeutic agents for multiple sclerosis in which the antibody or antigen binding portion thereof can be combined to include IFNβ, e.g., IFNβ1a and IFNβ1b, copaxone, corticosteroids, IL-1 inhibitors, TNF inhibitors, and antibodies to CD40 ligand and CD80.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may vary according to factors such as the disease state, age, sex, and weight of the individual, and the ability of the antibody or antibody portion to elicit a desired response in the individual. A therapeutically effective amount is also one in which any toxic or detrimental effects of the antibody or antibody portion are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.01-20 mg/kg, or 1-10 mg/kg, or 0.3-1 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

8. Uses of the Antibodies of the Invention 8.1. Anti-IL-12 Antibody Uses Generally Given their ability to bind to IL-12, the anti-IL-12 antibodies, or portions thereof, of the invention can be used to detect IL-12, in one aspect, hIL-12 (e.g., in a sample matrix, in one aspect, a biological sample, such as serum or plasma), using a conventional immunoassay, such as an enzyme linked immunosorbent assays (ELISA), an radioimmunoassay (RIA) or tissue immunohistochemistry. The invention provides a method for detecting IL-12 in a biological sample comprising contacting a sample with an antibody, or antibody portion, of the invention and detecting either the antibody (or antibody portion) bound to IL-12 or unbound antibody (or antibody portion), to thereby detect IL-12 in the sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 125I, 131I, 35S, or 3H. Detection of IL-12 in a sample may be useful in a diagnostic context, for example in the diagnosis of a condition associated with increased IL-12, and/or may be useful in identifying a subject who may benefit from treatment with an anti-IL-12 antibody.

Alternative to labeling the antibody, IL-12 can be assayed in a sample by a competition immunoassay utilizing, e.g., rhIL-12 standards labeled with a detectable substance and an unlabeled anti-IL-12 antibody, such as an anti-hIL-12 antibody. In this assay, the sample, the labeled rhIL-12 standards, and the anti-hIL-12 antibody are combined and the amount of labeled rhIL-12 standard bound to the unlabeled antibody is determined. The amount of hIL-12 in the sample is inversely proportional to the amount of labeled rhIL-12 standard bound to the anti-hIL-12 antibody.

The antibodies and antibody portions of the invention are capable of neutralizing IL-12 activity in vitro and in vivo, in one aspect, a hIL-12 activity. Accordingly, the antibodies and antibody portions of the invention can be used to inhibit IL-12 activity, e.g., in a cell culture containing IL-12, in human subjects or in other mammalian subjects having IL-12 with which an antibody of the invention cross-reacts (e.g., primates such as baboon, cynomolgus and rhesus). In a one aspect, the invention provides an isolated human antibody, or antigen-binding portion thereof, that neutralizes the activity of human IL-12, and at least one additional primate IL-12 selected from the group consisting of baboon IL-12, marmoset IL-12, chimpanzee IL-12, cynomolgus IL-12 and rhesus IL-12, but which does not neutralize the activity of the mouse IL-12. In one aspect, the IL-12 is human IL-12. For example, in a cell culture containing, or suspected of containing hIL- 12, an antibody or antibody portion of the invention can be added to the culture medium to inhibit hIL-12 activity in the culture.

In another aspect, the invention provides a method for inhibiting IL-12 activity in a subject suffering from a disorder in which IL-12 activity is detrimental. IL-12 has been implicated in the pathophysiology of a wide variety of disorders (Windhagen et al., (1995) J. Exp. Med. 182: 1985-1996; Morita et al. (1998) Arthritis and Rheumatism. 41: 306-314; Bucht et al., (1996) Clin. Exp. Immunol. 103: 347-367; Fais et al. (1994) J. Interferon Res. 14:235-238; Pyrronchi et al., (1997) Am. J. Path. 150:823-832; Monteleone et al., (1997) Gastroenterology. 112:1169-1178, and Berrebi et al., (1998) Am. J. Path 152:667-672; Pyrronchi et al. (1997) Am. J. Path. 150:823-832, the entire teachings of which are incorporated herein by reference). The invention provides methods for inhibiting IL-12 activity in a subject suffering from such a disorder, which method comprises administering to the subject an antibody or antibody portion of the invention such that IL-12 activity in the subject is inhibited. In one aspect, the IL-12 is human IL-12 and the subject is a human subject. Alternatively, the subject can be a mammal expressing IL-12 with which an antibody of the invention cross-reacts. Still further the subject can be a mammal into which has been introduced hIL-12 (e.g., by administration of hIL-12 or by expression of an hIL-12 transgene). An antibody of the invention can be administered to a human subject for therapeutic purposes. Moreover, an antibody of the invention can be administered to a non-human mammal expressing a IL-12 with which the antibody cross-reacts for veterinary purposes or as an animal model of human disease. Regarding the latter, such animal models may be useful for evaluating the therapeutic efficacy of antibodies of the invention (e.g., testing of dosages and time courses of administration).

As used herein, the phrase "a disorder in which IL-12 activity is detrimental" is intended to include diseases and other disorders in which the presence of IL-12 in a subject suffering from the disorder has been shown to be or is suspected of being either responsible for the pathophysiology of the disorder or a factor that contributes to a worsening of the disorder. Accordingly, a disorder in which IL-12 activity is detrimental is a disorder in which inhibition of IL-12 activity is expected to alleviate the symptoms and/or progression of the disorder. Such disorders may be evidenced, e.g., by an increase in the concentration of IL-12 in a biological fluid of a subject suffering from the disorder (e.g., an increase in the concentration of IL-12 in serum, plasma, synovial fluid, etc. of the subject), which can be detected, e.g., using an anti-IL-12 antibody as described above. There are numerous examples of disorders in which IL-12 activity is detrimental. In one aspect, the antibodies or antigen binding portions thereof, can be used in therapy to treat the diseases or disorders described herein. In another aspect, the antibodies or antigen binding portions thereof, can be used for the manufacture of a medicine for treating the diseases or disorders described herein. The use of the antibodies and antibody portions of the invention in the treatment of a few non-limiting specific disorders is discussed further below.

Interleukin 12 plays a critical role in the pathology associated with a variety of diseases involving immune and inflammatory elements. These diseases include, but are not limited to, rheumatoid arthritis, osteoarthritis, juvenile chronic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, atopic dermatitis, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpuria, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjodgren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycemia, type B insulin resistance with acanthosis nigricans, hypoparathyroidism, acute immune disease associated with organ transplantation, chronic immune disease associated with organ transplantation, osteoarthrosis, primary sclerosing cholangitis, idiopathic leucopenia, autoimmune neutropenia, renal disease NOS, glomerulonephritides, microscopic vasculitis of the kidneys, lyme disease, discoid lupus erythematosus, male infertility idiopathic or NOS, sperm autoimmunity, multiple sclerosis (all subtypes), insulin-dependent diabetes mellitus, sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Takayasu's disease/arteritis, autoimmune thrombocytopenia, idiopathic thrombocytopenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis and vitiligo. The human antibodies, and antibody portions of the invention can be used to treat autoimmune diseases, in particular those associated with inflammation, including, rheumatoid spondylitis, allergy, autoimmune diabetes, and autoimmune uveitis.

In certain aspects, the antibodies of the invention or antigen-binding portions thereof, are used to treat rheumatoid arthritis, Crohn's disease, multiple sclerosis, insulin dependent diabetes mellitus and psoriasis.

8.2 Use of Anti-IL-12 Antibody in Rheumatoid Arthritis

Interleukin-12 has been implicated in playing a role in inflammatory diseases such as rheumatoid arthritis. Inducible IL-12p40 message has been detected in synovia from rheumatoid arthritis patients and IL-12 has been shown to be present in the synovial fluids from patients with rheumatoid arthritis (see, e.g., Morita et al., (1998) Arthritis and Rheumatism 41: 306-314, the entire teaching of which is incorporated herein by reference). IL-12 positive cells have been found to be present in the sublining layer of the rheumatoid arthritis synovium. The human antibodies, and antibody portions of the invention can be used to treat, e.g., rheumatoid arthritis, juvenile rheumatoid arthritis, Lyme arthritis, rheumatoid spondylitis, osteoarthritis and gouty arthritis. Typically, the antibody, or antibody portion, is administered systemically, although for certain disorders, local administration of the antibody or antibody portion may be beneficial. An antibody, or antibody portion, of the invention also can be administered with one or more additional therapeutic agents useful in the treatment of autoimmune diseases.

In the collagen induced arthritis (CIA) murine model for rheumatoid arthritis, treatment of mice with an anti-IL-12 mAb (rat anti-mouse IL-12 monoclonal antibody, C17.15) prior to arthritis profoundly suppressed the onset, and reduced the incidence and severity of disease. Treatment with the anti-IL-12 mAb early after onset of arthritis reduced severity, but later treatment of the mice with the anti-IL-12 mAb after the onset of disease had minimal effect on disease severity.

8.3 Use of Anti-IL-12 Antibody in Crohn's Disease

Interleukin-12 also plays a role in the inflammatory bowel disease, Crohn's disease. Increased expression of IFN-γ and IL-12 occurs in the intestinal mucosa of patients with Crohn's disease (see, e.g., Fais et al., (1994) J. Interferon Res. 14: 235-238; Pyrronchi et al., (1997) Amer. J. Pathol. 150: 823-832; Monteleone et al., (1997) Gastroenterology 112: 1169-1178; Berrebi et al., (1998) Amer. J. Pathol. 152: 667-672, the entire teachings of which are incorporated herein by reference). Anti-IL-12 antibodies have been shown to suppress disease in mouse models of colitis, e.g., TNBS induced colitis IL-2 knockout mice, and recently in IL-10 knock-out mice. Accordingly, the antibodies, and antibody portions, of the invention, can be used in the treatment of inflammatory bowel diseases.

8.4 Use of Anti-IL-12 Antibody in Multiple Sclerosis

Interleukin-12 has been implicated as a key mediator of multiple sclerosis. Expression of the inducible IL-12 p40 message or IL-12 itself can be demonstrated in lesions of patients with multiple sclerosis (Windhagen et al., (1995) J. Exp. Med. 182: 1985-1996, Drulovic et al., (1997) J. Neurol. Sci. 147:145-150, the entire teachings of which are incorporated herein by reference). Chronic progressive patients with multiple sclerosis have elevated circulating levels of IL-12. Investigations with T-cells and antigen presenting cells (APCs) from patients with multiple sclerosis revealed a self-perpetuating series of immune interactions as the basis of progressive multiple sclerosis leading to a Th1-type immune response. Increased secretion of IFN-γ from the T cells led to increased IL-12 production by APCs, which perpetuated the cycle leading to a chronic state of a Th1-type immune activation and disease (Balashov et al., (1997) Proc. Natl. Acad. Sci. 94: 599-603, the entire teaching of which is incorporated herein by reference). The role of IL-12 in multiple sclerosis has been investigated using mouse and rat experimental allergic encephalomyelitis (EAE) models of multiple sclerosis. In a relapsing-remitting EAE model of multiple sclerosis in mice, pretreatment with anti-IL-12 mAb delayed paralysis and reduced clinical scores. Treatment with anti-IL-12 mAb at the peak of paralysis or during the subsequent remission period reduced clinical scores. Accordingly, the antibodies or antigen binding portions thereof of the invention nay serve to alleviate symptoms associated with multiple sclerosis in humans.

8.5 Use of Anti-IL-12 Antibody in Insulin-Dependent Diabetes Mellitus

Interleukin-12 has been implicated as an important mediator of insulin-dependent diabetes mellitus (IDDM). IDDM was induced in NOD mice by administration of IL-12, and anti-IL-12 antibodies were protective in an adoptive transfer model of IDDM. Early onset IDDM patients often experience a so-called "honeymoon period" during which some residual islet cell function is maintained. These residual islet cells produce insulin and regulate blood glucose levels better than administered insulin. Treatment of these early onset patients with an anti-IL-12 antibody may prevent further destruction of islet cells, thereby maintaining an endogenous source of insulin.

8.6 Use of Anti-IL-12 Antibody in Psoriasis

Interleukin-12 has been implicated as a key mediator in psoriasis. Psoriasis involves acute and chronic skin lesions that are associated with a TH 1-type cytokine expression profile. (Hamid et al. (1996) J. Allergy Clin. Immunol. 1:225-231; Turka et al. (1995) Mol. Med. 1:690-699, the entire teachings of which are incorporated herein by reference). IL-12 p35 and p40 mRNAs were detected in diseased human skin samples. Accordingly, the antibodies or antigen binding portions thereof of the invention may serve to alleviate chronic skin disorders such psoriasis.

8.7 Uses of Anti-IL-18 Antibody Generally

Given their ability to bind to IL-18, the anti-IL-18 antibodies, or portions thereof, of the invention can be used to detect IL-18, in one aspect, hIL-18 (e.g., in a sample matrix, in one aspect, a biological sample, such as serum or plasma), using a conventional immunoassay, such as an enzyme linked immunosorbent assays (ELISA), an radioimmunoassay (RIA) or tissue immunohistochemistry. The invention provides a method for detecting IL-18 in a biological sample comprising contacting a sample with an antibody, or antibody portion, of the invention and detecting either the antibody (or antibody portion) bound to IL-18 or unbound antibody (or antibody portion), to thereby detect IL-18 in the sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}$I, $^{131}$I, $^{35}$S, or $^{3}$H. Detection of IL-18 in a sample may be useful in a diagnostic context, for example in the diagnosis of a condition associated with increased IL-18, and/or may be useful in identifying a subject who may benefit from treatment with an anti-IL-18 antibody.

Alternative to labeling the antibody, IL-18 can be assayed in a sample by a competition immunoassay utilizing, e.g., rhIL-18 standards labeled with a detectable substance and an unlabeled anti-IL-18 antibody, such as an anti-hIL-18 antibody. In this assay, the sample, the labeled rhIL-18 standards, and the anti-hIL-18 antibody are combined and the amount of labeled rhIL-18 standard bound to the unlabeled antibody is determined. The amount of hIL-18 in the sample is inversely proportional to the amount of labeled rhIL-18 standard bound to the anti-hIL-18 antibody.

The antibodies and antibody portions of the invention are capable of neutralizing IL-18 activity in vitro and in vivo, in one aspect, a hIL-18 activity. Accordingly, the antibodies and antibody portions of the invention can be used to inhibit IL-18 activity, e.g., in a cell culture containing IL-18, in human subjects or in other mammalian subjects having IL-18 with which an antibody of the invention cross-reacts (e.g., primates such as baboon, cynomolgus and rhesus). In a one aspect, the invention provides an isolated human antibody, or antigen-binding portion thereof, that neutralizes the activity of human IL-18, and at least one additional primate IL-18 selected from the group consisting of baboon IL-18, marmoset IL-18, chimpanzee IL-18, cynomolgus IL-18 and rhesus IL-18, but which does not neutralize the activity of the mouse IL-18. In one aspect, the IL-18 is human IL-18. For example, in a cell culture containing, or suspected of containing hIL-18, an antibody or antibody portion of the invention can be added to the culture medium to inhibit hIL-18 activity in the culture.

In another aspect, the invention provides a method for inhibiting IL-18 activity in a subject suffering from a disorder in which IL-18 activity is detrimental. Interleukin 18 plays a critical role in the pathology associated with a variety of diseases involving immune and inflammatory elements.

As used herein, the phrase "a disorder in which IL-18 activity is detrimental" is intended to include diseases and other disorders in which the presence of IL-18 in a subject suffering from the disorder has been shown to be or is suspected of being either responsible for the pathophysiology of the disorder or a factor that contributes to a worsening of the disorder. Accordingly, a disorder in which IL-18 activity is detrimental is a disorder in which inhibition of IL-18 activity is expected to alleviate the symptoms and/or progression of the disorder. Such disorders may be evidenced, e.g., by an increase in the concentration of IL-18 in a biological fluid of a subject suffering from the disorder (e.g., an increase in the concentration of IL-18 in serum, plasma, synovial fluid, etc. of the subject), which can be detected, e.g., using an anti-IL-18 antibody as described above. There are numerous examples of disorders in which IL-18 activity is detrimental. In one aspect, the antibodies or antigen binding portions thereof, can be used in therapy to treat the diseases or disorders described herein. In another aspect, the antibodies or antigen binding portions thereof, can be used for the manufacture of a medicine for treating the diseases or disorders described herein. The use of the antibodies and antibody portions of the invention in the treatment of a few non-limiting specific disorders is discussed further below.

The invention provides pharmaceutical compositions for the treatment of diseases or conditions which require modulation of IL-18 activity. These diseases or conditions include autoimmune diseases, type I diabetes, rheumatoid arthritis, graft rejections, inflammatory bowel disease, sepsis, multiple sclerosis, ischemic heart diseases (including heart attacks), ischemic brain injury, chronic hepatitis, psoriasis, chronic pancreatitis, acute pancreatitis and the like.

Accordingly, anti-IL-18 antibodies or antigen-binding portions thereof, or vectors expressing same in vivo are indicated for the treatment of autoimmune diseases, Type I diabetes, rheumatoid arthritis, graft rejections, inflammatory bowel disease, sepsis, multiple sclerosis, ischemic heart disease including acute heart attacks, ischemic brain injury, chronic hepatitis, psoriasis, chronic pancreatitis and acute pancreatitis and similar diseases, in which there is an aberrant expression of IL-18, leading to an excess of IL-18 or in cases of complications due to exogenously administered IL-18.

8.8 Use Anti-IL-18 Antibody in Liver Injury

One aspect of the present invention is to provide for a novel means for treating and/or preventing liver injury. It has been found that an IL-18 inhibitor is effective in the prevention and treatment of liver damages. The invention therefore also relates to the use of an IL-18 inhibitor for the manufacture of a medicament for treatment and/or prevention of liver injury. More specifically, the invention relates to the treatment and/or prevention of liver injuries caused by alcoholic hepatitis, viral hepatitis, immune hepatitis, fulminant hepatitis, liver cirrhosis, and primary biliary cirrhosis.

8.9 Use Anti-IL-18 Antibody in Arthritis

It has also been found in accordance with the present invention that an inhibitor of IL-18 is effective in the therapy of arthritis. The therapeutic effect includes decreasing the severity of the disease, as well as preventing the spreading of the disease. The invention therefore relates to the use of an inhibitor of IL-18 for treatment and/or prevention of arthritis. This finding is unexpected, since from the state of the art outlined above, it could not have been concluded that a blockade of one specific factor involved in arthritis, namely interleukin IL-18, would lead to the alleviation of arthritis or even the curing of a diseased arthritic joint.

The term "arthritis" includes all different types of arthritis and arthritic conditions, both acute and chronic arthritis, as defined for example in the Homepage of the Department of Orthopaedics of the University of Washington on Arthritis. Examples for arthritic conditions are ankylosing spondylitis, back pain, carpal deposition syndrome, Ehlers-Danlos-Syndrome, gout, juvenile arthritis, lupus erythematosus, myositis, osteogenesis imperfecta, osteoporosis, polyarthritis, polymyositis, psoriatic arthritis, Reiter's syndrome, scleroderma, arthritis with bowel disease, Behcets's disease, children's arthritis, degenerative joint disease, fibromyalgia, infectious arthritis, Lyme disease, Marfan syndrome, osteoarthritis, osteonecrosis, Pagets Disease, Polymyalgia rheumatica, pseudogout, reflex sympathetic dystrophy, rheumatoid arthritis, rheumatism, Sjogren's syndrome, familial adenomatous polyposis and the like.

Rheumatoid arthritis (RA) causes inflammation in the lining of the joints (the synovial membrane, a one cell layer epithelium) and/or internal organs. The disease tends to persist for many years, typically affects many different joints throughout the body and ultimately can cause damage to cartilage, bone, tendons, and ligaments. The joints that may be affected by RA are the joints located in the neck, shoulders, elbows, hips, wrists, hands, knees, ankles and feet, for example. In many cases, the joints are inflamed in a symmetrical pattern in RA.

RA is prevalent in about 1% of the population in the United States, being distributed within all ethnic groups and ages. It occurs all over the world, and women outnumber men by 3 to 1 among those having RA.

It has been found that the administration of an IL-18 inhibitor significantly diminishes cartilage erosion in a murine model of arthritis. The present invention thus also relates to the use of an inhibitor of IL-18 in the manufacture of a medicament for treatment and/or prevention of cartilage destruction.

8.10 Use of anti-TNFα Antibody Generally

Tumor necrosis factor-α is a multifunctional pro-inflammatory cytokine secreted predominantly by monocytes/macrophages that has effects on lipid metabolism, coagulation, insulin resistance, and endothelial function. TNFα is a soluble homotrimer of 17 kD protein subunits. A membrane-bound 26 kD precursor form of TNFα also exists. It is found in synovial cells and macrophages in tissues. Cells other than monocytes or macrophages also produce TNFα. For example, human non-monocytic tumor cell lines produce TNFα as well as CD4$^+$ and CD8$^+$ peripheral blood T lymphocytes and some cultured T and B cell lines produce TNFα. It is involved in, but not unique to, rheumatoid arthritis, and occurs in many inflammatory diseases. Receptors for TNFα are on several mononuclear cells, in the synovial membrane, as well as the peripheral blood and synovial fluid. TNFα is a critical inflammatory mediator in rheumatoid arthritis, and may therefore be a useful target for specific immunotherapy.

TNFα causes pro-inflammatory actions which result in tissue injury, such as degradation of cartilage and bone, induction of adhesion molecules, inducing pro-coagulant activity on vascular endothelial cells, increasing the adherence of neutrophils and lymphocytes, and stimulating the release of platelet activating factor from macrophages, neutrophils and vascular endothelial cells. Recent evidence associates TNFα with infections, immune disorders, neoplastic pathologies, autoimmune pathologies and graft-versus-host pathologies.

TNFα is believed to play a central role in gram-negative sepsis and endotoxic shock, including fever, malaise, anorexia, and cachexia. Endotoxin strongly activates monocyte/macrophage production and secretion of TNFα and other cytokines. TNFα and other monocyte-derived cytokines mediate the metabolic and neurohormonal responses to endotoxin. Endotoxin administration to human volunteers produces acute illness with flu-like symptoms including fever, tachycardia, increased metabolic rate and stress hormone release. Circulating TNFα increases in patients suffering from gram-negative sepsis.

Thus, TNFα has been implicated in inflammatory diseases, autoimmune diseases, viral, bacterial and parasitic infections, malignancies, and/or neurodegenerative diseases and is a useful target for specific biological therapy in diseases, such as rheumatoid arthritis and Crohn's disease. Beneficial effects in open-label trials with a chimeric monoclonal antibody to TNFα have been reported with suppression of inflammation and with successful re-treatment after relapse in rheumatoid arthritis and in Crohn's disease.

Neutralizing antisera or mAbs to TNFα have been shown in mammals to abrogate adverse physiological changes and prevent death after lethal challenge in experimental endotoxemia and bacteremia. Adalimumab (also known by its trademark HUMIRA® available from Abbott Laboratories) is a recombinant human monoclonal antibody specific for TNFα. This monoclonal antibody binds to TNFα and blocks its interaction with the p55 and p75 cell-surface TNFα receptors. This monoclonal antibody is quite specific for TNFα as it appears not to inhibit the activity of TNFβ. In the presence of complement, adalimumab lyses the surface of cells expressing TNFα.

EXAMPLES

1. The Isolation And Purification of Anti-IL-12 Antibody 1.1 Purification Strategy Upon completion of a production cell culture operation designed to produce IL-12 antibodies, the broth was slowly adjusted to and maintained at pH 3.5 for a period of 1 hour, then readjusted to pH 5, followed by centrifugation (11,000× g) to remove cells and precipitated impurities. The centrifugation supernatant was further clarified by a two step filtration train (Cuno 90ZA depth filtration, followed by 0.45/0.2 μm filtration). Following clarification, the antibody was captured and further purified in a five step procedure.

The clarified acidified cell culture harvest was titrated to pH 7 with 3 N NaOH in the course of 30 minutes and filtered prior to chromatography.

A 1.0 cm diameter×21.6 cm long column (17 mL bed volume) was used for this operation at the bench scale. A 1.0 cm×15.1 cm column (11.9 mL bed volume) was used at the early stage to generate material for the fine purification development. A 20 cm×21 cm column (6.6 L bed volume) was used at the 300 L scale. The columns were packed with MabSelect™ resin (GE Healthcare, cat#17-5199-04, lot#302070); the asymmetry and Height of an Equivalent Theoretical Plate (HETP) were measured to determine the quality of the packing.

The column was pre-equilibrated with 25 mM Tris, 100 mM NaCl, pH 7.2 buffer. Following equilibration, the column was loaded with clarified cell culture harvest (v=300 cm/hr for the initial 35 g Ab/L resin load, then 150 cm/hr till the end of the load, 40 g/L maximum). The column was then washed with 3 column volumes (CV) of equilibration buffer (v=300 cm/hr) followed by 3 CVs of 20 mM citric acid/NaCltrate, 0.5 M NaCl, pH 6 buffer wash, followed by an additional 3 CVs of equilibration buffer. The product was then eluted with 0.1 M acetic acid, 100 mM NaCl, pH 3.5 (v=300 cm/hr). The column eluate was collected from an initial $A_{280}$ deflection of 0.1 AU to a reading of 0.1 AU at the trailing edge of the elution peak (2 mm flow cell path) and titrated to pH 5 immediately with 1.0 M Tris, pH 10 buffer.

The dynamic binding capacity (DBC) of the MabSelect™ column was determined either by a single flow rate load or dual-flow rate load strategy. The single flow rate load was evaluated at 300 cm/hr through the entire loading. The dual-flow rate load strategy was carried by loading the column up to 35 mg protein/mL resin at a linear velocity of 300 cm/hr, and then reducing the linear velocity by half to allow longer residence time for the last portion of the load. In each experiment the column was overloaded to ensure the saturation of the column at the given loading conditions. The flow-through material for each run was fractionated to determine the total amount of antibody loaded before 5% was detected in the break though. Titers of flow through (FT) fractions were obtained by the Poros A™ HPLC assay.

Recovery was calculated by UV spectrophotometry at 280 nm (extinction coefficient of 1.42 for a 1 mg/mL solution using a 1 cm path length) for elution samples. Titers of the load were determined by the Poros A™ HPLC assay. SEC-HPLC, HCP ELISA and Protein A ELISA were carried out for purity assessment, HCP removal and leached Protein A levels.

The MabSelect™ eluate was titrated to pH 8±0.1 with 1 M Tris buffer, pH 10, and then diluted to 6.5±0.5 mS/cm with water. The diluted material was mixed for a period of one hour, followed by a Cuno™ delipid and 0.45/0.22 μm filtration.

A 1.0 cm diameter×29 cm long column (22.8 mL bed volume) was used for the Q Sepharose™ Fast Flow chromatography at the bench scale. A 20 cm×29.5 cm column (9.27 L bed volume) was used at the 300 L scale. The columns were packed with Q Sepharose™ FF resin (GE Healthcare, Piscataway, N.J., cat#17-0510-04, lot#296307 for the 300 L scale, lot#303189 for the bench scale); asymmetry and HETP were measured to determine the quality of the packing.

Equilibration of the resin was accomplished with 25 mM Tris, 50 mM NaCl, pH 8. The chromatography was operated in the flow-through mode where process-related impurities adsorbed to the resin and antibodies flowed through the column. Loading of the column was performed at 150 cm/hr, and the column flow-through (FTW) collection was started when the $A_{280}$ rose above 0.2 AU. Samples of the FTW material were taken at intervals corresponding to 30, 50, 80, 90 and 100 g of protein/L resin loadings. The column was then washed with equilibration buffer and the FTW collection was continued until the $A_{280}$ returned to an OD of 0.2 AU. The Q Sepharose™ FTW was diluted with an equal volume of 1.7 M $(NH_4)_2SO_4$, 50 mM Na phosphate, pH 7 (SR-343) immediately, to prepare for loading onto the Phenyl Sepharos™e HP column. This solution was 0.2 µm filtered and labeled Phenyl Sepharose™ HP load.

Recovery was calculated by UV spectrophotometry at 280 nm (extinction coefficient of 1.42 for a 1 mg/mL solution using a 1 cm path length). SEC-HPLC, HCP ELISA and Protein A ELISA were carried out for purity assessment, HCP removal and leached Protein A removal.

A 1.0 cm diameter×15.6 cm long column (12.3 mL bed volume) was used for Phenyl Sepharose™ HP Chromatography at the bench scale. A 20 cm×15.5 cm column (4.87 L bed volume) was used at the 300 L scale. The columns were packed with Phenyl Sepharose™ HP resin (GE Healthcare, Piscatway, N.J., cat#17-1082-04, lot#298138); asymmetry and HETP were measured to determine the quality of the packing.

Equilibration of the resin was accomplished with 25 mM sodium phosphate, 0.85 M ammonium sulfate, pH 7. The maximum protein loading for this step was <40 g protein per liter of resin (v=75 cm/hr). Following loading, the column was washed with 3 column volumes of 20 mM sodium phosphate, 1.1 M $(NH_4)_2SO_4$, pH 7 (SR-290). The product was eluted by performing a step gradient using 15 mM sodium phosphate, pH 7, 0.5 M ammonium sulfate at a linear velocity of 37.5 cm/hr. The column eluate was collected from an initial $A_{280}$ deflection of 1.0 AU to a reading of 0.2 AU at the trailing edge of the elution peak. Aggregates and other impurities remain bound to the resin and were stripped off the HIC column by washing with water or 0.5 M NaOH.

Recovery was calculated by UV spectrophotometry at 280 nm (extinction coefficient of 1.42 for a 1 mg/mL solution using a 1 cm path length). SEC-HPLC, HCP ELISA and Protein A ELISA were carried for purity assessment, HCP removal and leached Protein A removal.

Viral filtration with the Ultipor DV20™ filter was not evaluated at either the bench scale or the scale-up lab due to the size limitation at both scales. Instead, an Ultipor DV50™ filter was used at the 300 L scale to generate the pre-clinical material. At the bench scale, the product that eluted from the Phenyl Sepharose™ HP chromatography was used directly for the final ultrafiltration and diafiltration operation.

A Millipore 30 kD molecular weight cut-off (MWCO) regenerated cellulose ultrafilter was used for this step (UF/DF). Prior to operation, the UF system was sanitized with 1 M NaOH and rinsed with water.

The DV50™ filtrate was initially concentrated to 30 mg/mL protein. Continuous diafiltration with 2 volumes (DV) of 5 mM histidine, 5 mM methionine, 0.5% sucrose, 2% (w/v) mannitol, pH 5.9 (diafiltration buffer) (SR-265) was performed. The retentate was further concentrated to 40 g/L, then diafiltrated with an additional 6 DVs of diafiltration buffer. The retentate was further concentrated to ~75 g/L. The UF system was then drained of product and rinsed with diafiltration buffer to recover product held up in the system. The concentrate and wash were combined to produce the diafiltered antibody product at ~65 g/L. This product was 0.2 µm filtered and ready for final bottling.

1.2 Analysis of Sample Purity

SEC-HPLC. The purity of the antibody product was assessed by size-exclusion chromatography SEC-HPLC.

Poros A HPLC Assay. The antibody titers of the harvest, MabSelect™ load and flow through samples were determined by a Poros A™ quantitation capture assay.

HCP ELISA. Host cell protein levels were evaluated using Host Cell Protein-ELISA. HCP was sandwiched between two specific antibodies in an Enzyme Linked Immunosorbant Assay (ELISA).

The plate was coated with a 100 µL/well of a mixture of goat anti CHO affinity purified antibodies (6 µg/mL each in 50 mM sodium bicarbonate, pH 9.4) for 1 hour at 37° C. while shaking at 80 rpm; the contents of the plate were then poured out and non-specific sites were blocked with 300 µL/well of casein for 1 hour at 37° C. while shaking at 80 rpm. After blocking, the plate was washed with wash buffer (1×PBS, 0.1% Triton X-100, pH 9). Samples for the standard curve were prepared from serially diluting a 5.2 mg/mL aliquot of CHO host cell proteins. The diluent for all reagents was casein, heated to 37° C. and sonicated for 2 minutes, unless otherwise stated. Concentrations for the standard curve were 300, 200, 133, 89, 59, 40, 26, and 18 ng/mL. Antibody standard was diluted 5× and used as the assay control. For the assay to be accepted, the calculated value for the control must be in the range of 45-76 ng HCP/mL. Samples were diluted so that the calculated values would fall within the range of the standard curve. Standards, control, and samples (100 µL/well) were loaded onto the plate in duplicate. The plate was incubated at 37° C. while shaking at 80 rpm for 1 hour. After sample incubation, the plate was washed with buffer and loaded with 100 µL/well of biotinylated goat anti CHO antibody diluted to 3 µg/mL. The plate was incubated at 37° C. while shaking at 80 rpm for 1 hour and then washed. 100 µL/well of Neutravadin-Hoorse Rsadish Peroxidase (HRP) at 100 µg/mL was added and the plate incubated at 37° C. while shaking at 80 rpm for 1 hour. A final wash was performed and the plate was developed with 100 µL/well of K Blue HRP colorometric substrate for 7 minutes while shaking at speed 3 on a Lab-line titer plate shaker at room temperature. The reaction was stopped with the addition of 100 µL/well of 2 M phosphoric acid and the plate was read at 450 nm. Color development is proportional to the amount of HCP present in the test sample.

Protein A ELISA. Protein A clearance was evaluated using an assay kit from Cygnus Technologies, Inc. (Immunoenymetric Assay for the Measurement of Protein A in samples containing human immunoglobulin, catalog#F050H). Standards, reagents, and plate were provided in the kit. Samples were diluted to 1 mg/mL with 1×PBS and denatured at 100° C. for 5 minutes with denaturing buffer (50 µL denaturing buffer into 200 µL, sample). The samples were centrifuged at 6000×g for 5 minutes to pellet the denatured antibody. 100 µL of biotinylated anti-Protein A and 50 µL of supernatant from denatured samples, controls, and standards were added to all wells. The plate was incubated for 1 hour at room temperature while shaking at 180 rpm. The contents of wells were aspirated and the plate manually washed four times with 300 μL of wash solution. Streptavidin:Alkaline Phosphatase was added to each well (100 μL) and the plate was incubated at room temperature for 1 hour while shaking at 180 rpm. After washing the plate as described above, 100 μL of Alkaline Phosphatase colorometric substrate was added to the wells and the plate was incubated for 30 minutes at room temperature while shaking at 180 rpm. The plate was read at 405 and 492 nm. If the absorbance for the 16 ng/mL sample was <1.2, the plate was incubated an additional 30 minutes and re-read. Color development is proportional to the amount of Protein A present in the test sample.

1.3 Results of Purification Strategy

Protein A chromatography. The MabSelect™ Protein A chromatography was used to capture anti-IL-12 antibodies and reduce product and process related impurities such as single and double light chain fragments, CHO host cell proteins (HCPs) and DNA, etc. Data from both bench scale and 300 L bioreactor scale showed good protein recovery and HCP clearance (Tables 1 and 2). A representative chromatogram from the 300 L bioreactor scale was provided in FIG. 4.

TABLE 1

Summary of recovery and purity for the new process at bench-scale

| Process step | Recovery (%) | Purity (% monomer) | HCP (ng/mg Ab)* | Leached Protein A (ng/mg Ab) |
|---|---|---|---|---|
| Clarification | 91 | ND** | 211195.7 | 0.14 |
| MabSelect ™ | 95 | 97.5 | 1121.9 | 9.36 |
| Q Seph ™ FF | 96 | 96.9 | 34.5 | 8.21 |
| Phenyl HP | 90 | 99.2 | 11.1 | 0.65 |
| Overall | 81 | ND** | ND** | ND** |

*1 Day HCP ELISA assay. SOP PD-122.
**ND—not determined.

TABLE 2

Summary of the new process at 300 liter scale

| Process step | Recovery (%) | Purity (% monomer) | HCP (ng/mg Ab)* | Leached Protein A (ng/mg Ab) |
|---|---|---|---|---|
| Clarification | 91 | ND** | 141753 | ND** |
| MabSelect ™ | 95 | 94.44 | <2117.6 | 7.6 |
| Delipid filtration | 97 | 95.97 | 58 | 3.4 |
| Q Seph ™ FF | 93 | 96.21 | 8 | 3.7 |
| Phenyl Seph ™ HP | 92 | 99.72 | 4 | 2.3 |
| DV50 ™ | 95 | 99.64 | ND** | ND** |
| UF/DF | 99 | 99.59 | ND** | ND** |
| Bottling | 99 | 99.55 | 5 | 0.3 |
| Overall | 67 | NA*** | NA*** | NA*** |

*1 Day HCP ELISA assay, SOP PD-122.
**ND = not determined.
***NA = not applicable.

Data shown in Table 3 demonstrated that the dynamic binding capacity of the MabSelect™ chromatography was affected by load flow rate, specifically by residence time. When loaded at a constant linear velocity of 300 cm/hr (3.4 minutes residence time), the DBC was 44.3 mg protein/mL resin. When the dual-flow rate loading strategy (300 cm/hr up to 35 g/L, switching to 150 cm/hr resulted in the DBC increasing by 17% to 51.7 mg protein/mL resin. This increase of the DBC was accomplished by doubling residence time for the latter portion of the load. Theoretically, in the initial stage of column loading, binding occurs predominately at the bead surface, sites which are easily accessible. This permits the use of faster flow rates with little impact on binding kinetics. Once all the readily accessible sites are occupied, proteins need to diffuse into pores to bind to the less readily accessible sites. Kinetically this is a slower process and therefore, the flow rates should be reduced accordingly to maximize binding.

TABLE 3

Effect of flow rate on the DBC of the MabSelect ™ column

| | Load linear velocity | Experiment # | DBC at 5% BT (mg Ab/mL resin) |
|---|---|---|---|
| Single flow rate load | 300 cm/hr | Exp. 1 | 43.7 |
| | | Exp. 2 | 44.9 |
| | | Average | 44.3 |
| Dual-flow rate load | Initial linear velocity of 300 cm/hr till 35 mg Ab/mL resin load, 2nd linear velocity of 150 cm/hr until appearance of antibody in the load flow through | Exp. 3 | 51.6 |
| | | Exp. 4 | 51.7 |
| | | Average | 51.7 |

The double light chain amount was reduced from 0.5% to 0.2% (according to HPLC-SEC) by implementing an intermediate wash step. Several wash buffers were evaluated including 0.5 M NaCl, 25 mM sodium acetate, 0.5 M NaCl, pH 5.0 or pH 5.5 and 20 mM citric acid/Na citrate, 0.5 M NaCl, pH 6. Data from both HPLC-SEC and SDS-PAGE (FIG. 5) showed a good clearance of low molecular weight (LMW) species from all the experiments. When the wash was performed at pH 6, the same clearance of LMW was observed compared to the lower pH washes, while the 95% protein recovery was comparable to runs without the intermediate wash step.

Q Sepharose™ Fast Flow chromatography. The Q Sepharose™ FF column was used to reduce negatively charged process and product related impurities such as DNA and host cell proteins. This and subsequent steps constitute the fine purification steps in the overall process.

Prior to the chromatography, load sample preparation began with the adjustment of the pH and conductivity of the MabSelect™ eluate. The pH of the eluate was adjusted from pH 5 to pH 8 using 1 M Tris, pH 10; immediately followed by a lowering of the conductivity from ~15 mS to 7 mS with water. Once the conductivity of MabSelect™ eluate approached 7 mS/cm, precipitation started to occur and was allowed to continue for one hour. The precipitated material was removed by a Cuno™ delipid or 30ZA depth filter, followed by a 0.45/0.2 μm filtration. Protein recovery of this load preparation step was 96.3% according to the UV absorbance at 280 nm, indicating that the majority of the precipitated material was not antibody. This was also confirmed by SDS-PAGE analysis of the precipitates (FIG. 6).

The Q Sepharose™ FF column was operated in a flow through mode. A representative chromatography profile is shown in FIG. 7. No apparent break though of HCPs were observed when loaded at 80 g Ab/L resin at the 300 L bioreactor scale (Table 4). Once the loading reached 90 g Ab/L resin, the HCP level doubled in the flow through wash (FTW), indicating that the resin was reaching its binding capacity. HCP levels continued to increase at 100 g Ab/L resin loading (Table 4). This represents a significant improvement over the current antibody manufacturing process. Maximum loading is 50 g Ab/L resin. This loading represents a 60% increase of the binding capacity for the Q Sepharose™ operation. The increase in load capacity is due to the use of an affinity resin such as Protein A vs. a cation exchanger for the capture step, resulting in much cleaner feed streams for the Q Sepharose™ unit operation.

The protein recovery is typically high for this step. Data from both bench and the 300 L bioreactor scale runs resulted in comparable step yields (96% and 93%) (Tables 1 and 2). HCP reduction (97% and 85%) was also achieved at both scales (Tables 1 and 2).

TABLE 4

Effect of load amount on HCP clearance of the QFF column

| Q load amount | HCP (ng/mL)* | Ab (mg/mL) | HCP (ng/mg) |
|---|---|---|---|
| Q load depth filtered | 436.306 | 7.54 | 58 |
| Q FTW 30% load** | 104.122 | 8.66 | 12 |
| Q FTW 50% load** | 61.642 | 8.59 | 7 |
| Q FTW 80% load** | 61.867 | 8.80 | 7 |
| Q FTW 90% load** | 132.955 | 8.80 | 15 |
| Q FTW 100% load** | 157.683 | 8.52 | 17 |
| Q FTW pool | 62.808 | 8.24 | 8 |

*1 day HCP ELISA assay, SOP PD-122.
**100% load = 100 g Ab/L resin load.

HIC chromatography. HIC chromatography was used to remove aggregated and fragmented antibody molecules from the intact antibodies based on their differences in hydrophobicity. In the case of anti-IL-12 antibodies, aggregates are more hydrophobic than the monomers, hence bound tighter to the HIC column. When the column is eluted with 0.5M ammonium sulfate, monomeric Ab is eluted off, whereas aggregates remain bound to the column and come off only in the water strip. In contrast, the fragmented antibody molecules or low molecular weigh species (LMW) are less hydrophobic than the intact antibodies and hence are not bound as tightly to the HIC chromatography resin. Most of the LMW are eluted off the column prior to the main elution peak. Since the upstream MabSelect™ wash step was able to remove a majority of the LMW from the process stream; the HIC process was designed mainly to remove aggregated antibodies, Protein A leachables, residual HCPs and other process and product related impurities to achieve final product specifications. A representative chromatography elution profile is provided in FIG. 8.

Data from both the bench and 300 L scale showed 90% recovery, and good aggregate removal (>99% purity) by HIC chromatography (see Tables 1 and 2). Leached Protein A in the Q FTW material was reduced from 8.21 to 0.65 ng/mg Ab (ppm) by the HIC chromatography operation (see Table 1).

In comparison to the current manufacturing process (e.g., cation exchange capture), Protein A affinity capture based process was able to purify anti-IL-12 antibodies from CHO cell culture harvest with a higher yield and better HCP removal.

2 The Isolation and Purification of anti-TNFα Antibody
2.1 The Purification Strategy Cell Culture Harvest Clarification. Cell culture day 13 fermentation harvest broth and a clarified day 15 fermentation harvest material were used as starting material in this example. Cell culture broth was centrifuged at 3000 rpm for 30 minutes with Beckman Coulter Allegra™ 6R Centrifuge. The collected supernatant was filtered through Delipid filter (CUNO ZeraPlus® BC0030A DELI-BioCap™ 30 disposable capsule) at flow rate of 20 mL/min. The clarified harvest was then aliquoted and stored at −80° C. The frozen harvest was thawed and filtered with a 0.22 µm Corning® Cellulose Acetate filter before loading on to the column. The harvest broth was centrifuged with a disc-stack centrifuge and further filtered through depth filter and delipid filter. The filtrate was stored at 4° C. before loading on the column. The clarification process was performed at room temperature.

Protein A Affinity Chromatography. A 10 mL (1.6×5 cm) column and a 40.2 mL (1.6×20 cm) column were packed with MabSelect™ resin (GE Healthcare). An AKTA Explorer™ chromatography system was used for the operations. Column were packed using 0.5 M NaCl. Table 5 displays the chromatography conditions. The elution peak fractions were combined and held for 1 hour before being neutralized to pH 8.0 with 3M Trolamine. The process was performed at room temperature.

TABLE 5

Protein A affinity Chromatography conditions

| Step | Solution | Volume (CV) | Linear Velocity* (cm/h) |
|---|---|---|---|
| Rinse | Water | 5 | 400 |
| Equilibration | 1 × PBS | 5 | 400 |
| Load | See sample info | variable | 400 |
| Wash | 1 × PBS | 5 | 400 |
| Elution | Acetic acid buffer w/pH 3.2 | 5 | 400 |
| regeneration | 1.0% Acetic Acid/0.5M NaCl | 5 | 400 |
| sanitization every cycle | 6.0M Guanidine | 5 | 100 |
| Rinse | Milli Q Water | 5 | 400 |
| Storage | 50 mM Na Acetate pH5, 20% ethanol | 3 | 100 |

*Linear velocity was 100 cm/h for 5 cm height column and 400 cm/h for 20 cm height column to keep the same residence time.

Q Load Material Preparation. The neutralized eluate from two Protein A runs were combined and diluted with approximately 0.5~1.0 time with Milli Q water to achieve a conductivity of 4.5~5.5 mS/cm (25° C.). The diluted sample was filtered through a depth filter (CUNO Zeta Plus BioCap® BC0030A30ZA) at a flow rate of 20 mL/min followed with a 0.45 µm cellulose acetate filter (Corning, Inc.) and then 0.22 µm cellulose acetate filter (Corning, Inc.). The sample was then ready to load onto the Q column.

Q Sepharose™ Anion Exchange Chromatography. A 60.3 mL (1.6×30m) and a 40.2 mL (1.6×20 m) column were packed with Q Sepharose™ Fast Flow resin (GE Healthcare) and operated by AKTA Explorer™ chromatoragphy system. Table 6 displays the chromatography conditions. The process was performed at 12° C. Column flow through samples were collected for Phenyl HP chromatography purification.

TABLE 6

Q Sepharoses chromatography condition

| Step | Solution | Volume (CV) | Linear Velocity (cm/h) |
|---|---|---|---|
| Equilibration | 25 mM Trolamine, 40 mM NaCl, pH 8.0 | 5 | 149 |
| Load | See sample info | variable | 149 |
| Wash | 25 mM Trolamine, 40 mM NaCl, pH 8 | 5 | 149 |
| Regeneration | 25 mM NaPi, 1M NaCl, pH 7.0 | 3 | 149 |
| Rinse | WFI water | 2 | 149 |
| Sanitize | 1M NaOH | 3 | 74.6 |
| Rinse | WFI water | 3 | 74.6 |
| Storage | 25 mM NaPi, 20% iPrOH | 5 | 74.6 |

Phenyl Sepharose™ HP Chromatography. A 30.2 mL (1.6×15 cm) column was packed with Phenyl Sepharose™ HP resin (GE Healthcare) and operated by AKTA Explorer chromatography system. The Q flow through was diluted with 2.2 M (NH4)$_2$SO$_4$/40 mM NaH$_2$PO$_4$ buffer at 1:1 ratio to achieve a conductivity of 147±11 mS/cm for loading onto Phenyl Sepharose™ HP column. The main elution peak was collected. Table 7 displays the chromatography conditions. The process was performed at 12° C.

TABLE 7

Phenyl HP chromatography condition

| Step | Solution | Volume (CV) | Linear Velocity (cm/h) |
|---|---|---|---|
| Equilibration | 1.1M(NH4)SO4, 20 mM Na-PO4 | 5 | 75 |
| Load | See sample info | variable | 75 |
| Wash | 1.1M(NH4)SO4, 20 mM Na-PO4 | 5 | 75 |
| Elution | 0.6M-0.65M AmSO4, 11.4 mM NaPi | 3 | 37.5 |
| Regeneration | 25 mM Na-PO4, 20% iPrOH | 3 | 37.5 |
| Rinse | Milli Q water | 3 | 37.5 |
| Sanitization | 1M NaOH | 3 | 37.5 |

2.2 Analysis of Sample Purity pH. A pH meter was calibrated using two pH standard solutions (pH 4 and 7 or pH 7 and 10) immediately before use. The measured values were within the calibration points. A Corning Pinnacle 545 pH meter was used.

Conductivity. Conductivity was measured at 25° C., using a Radiometer Analytical CDM210 conductivity meter.

UV spectroscopy $A_{280}$ UV $A_{280}$ was measured, using an Agilent UV8453 spectrophotometer. The extinction coefficient used for adalimumab is 1.39 L/g·cm.

Poros A HPLC. Antibody concentration was determined by Poros A (Protein A) HPLC. Sample dilutions were applied to achieve readings within the calibration range. A Shimadzu HPLC system was configured with a Poros A ImmunoDetection sensor cartridge (Applied Biosystems, Foster City, Calif.). The column was maintained at ambient temperature. The system was run at 2 mL/minute. Autosampler tray temperature was set at 4° C. Absorbance was monitored at 280 nm. Buffer A was 1×PBS. Buffer B was 0.1 M acetic acid and 150 mM sodium chloride. The sample was injected and adalimumab was eluted using 100% Buffer B.

WCX-10 HPLC. WCX-10 HPLC (weak cation exchange) analysis was performed. A Shimadzu HPLC system was configured with a Dionex ProPac WCX-10 analytical column and a guard column (Dionex Corporation, Sunnyvale, Calif.). Both columns were maintained at 30° C. The system was run at 1 mL/minute. Auto sampler tray temperature was set at 4° C. Absorbance was monitored at 280 nm. Buffer A was 10 mM sodium phosphate dibasic, pH 7.5 and Buffer B was 10 mM sodium phosphate dibasic/500 mM sodium chloride, pH 5.5. The sample was injected and adalimumab was eluted using the gradient method as following.

| Time (min) | Buffer A (%) | Buffer B (%) |
|---|---|---|
| 0.0 | 94 | 6 |
| 20.0 | 84 | 16 |
| 22.0 | 0 | 100 |
| 26.0 | 0 | 100 |
| 28.0 | 94 | 6 |
| 34.0 | 94 | 6 |

Size exclusion Chromatography (SEC) HPLC. SEC analysis was performed. Sample dilutions were applied to achieve readings within the standard curve. A Shimadzu HPLC system was configured with a Superose™ 6 10/300 GL column (GE Healthcare). The column was maintained at ambient temperature. The system was run at 0.5 mL/minute. Autosampler tray temperature was set at 4° C. Absorbance was monitored at 214 nm. Buffer A was 20 mM sodium phosphate dibasic/150 mM sodium chloride. The sample was injected and adalimumab was run isocratically using 100% Buffer A.

HCP ELISA. HCP ELISA was performed as outlined above. Sample dilutions were applied to achieve readings within the calibration range.

Protein A ELISA assay. Leachable Protein A concentration analysis was performed as outlined above. Immunoenzymetric Assay for the Measurement of Protein A samples containing human immunoglobulin assay pre-coated kits (Catalog #F050H) including the sample diluent (Catalog #1028) were purchased from Cygnus Technologies, Inc. Block heater (Type 17600 Dry-Bath, Barnstead/Thermolyne) was used for sample denaturing. Incubator (max 4000, Barnstead/LabLine) was used for sample incubation. Plate reader (Spectramax Plus, Molecular Devices) was used for absorbance reading at 405 nm and 495 nm.

SDS-PAGE. Samples were diluted with 1×PBS buffer to a designed concentration, then an equal volume of 2× loading buffer (Invitrogen Novex® Tris-Glycine SDS Sample Buffer (2×), Cat#LC2676) was added to each diluted sample. For reducing SDS-PAGE, one tenth volume of reducer (invitrogen™ NaPAGE® Sample Reducing Agent (10×), Cat#NP0004) was added into each sample. 20 μL of each prepared sample was loaded in each well on the gel (invitrogen 12% Tris-Glycine Gel). The gel was run under 1× Tri-Glycine-SDS running buffer (diluted from 10× Tris-Glycine-SDS buffer from ABC Storage Room) at constant voltage of 125 V and 35 mA for 108 minutes. SimpleBlue™ SafeStain (invitrogen™, Cat#LC6060) was used to stain the gel for 2 hours and destained with Milli Q water until clear bends appeared. SeeBlue® Plus Prestained Standard (1×) (invitrogen Cat#LC5925) was used as a marker in this study. Each prepared sample was loaded on the base of equal total amount of antibody.

2.3 Results of Purification Strategy

MabSelect™ Dynamic Binding Capacity. The dynamic binding capacity of a resin under given conditions can be estimated by over-loading the column and analyzing the resultant breakthrough of product. Typically, the setting for maximum binding capacity is to determine the loading corresponding to 10% breakthrough and then reducing this by 10 to 20% as a safety margin to assure that process measurement variability and the Protein A ligand leached with the time to be covered. The 10% breakthrough point for MabSelect™ resin is at 37.4 g antibody per L of resin (FIG. 9). This suggested a maximum recommended resin binding capacity of 32 g/L resin at a flow rate of 400 cm/hr under the studied conditions. 32 g/L load amount was used in this example.

Antibody Recovery Yield. There were two runs performed for product yield and quality study. Harvest broth were clarified as described above. Filtrates were loaded onto the MabSelect™ column and run as described above. The eluates pH (pH 4.06) were higher than the sufficient viral reduction/inactivation pH (pH 3.5), therefore the eluate pool was adjusted to pH 3.5 with 10× diluted glacial acetic acid (J. T. Baker 9522-03). In the Q Sepharose™ chromatograph step, 30 g/L were loaded in Run 1 and 40 g/L in Run 2 to challenge the impurity clearance capability of the process.

Table 8 listed the antibody recovery step yields from these 2 runs and a process for purification not employing Protein A ("AY-04").

TABLE 8

Recovery yields in the studied Protein A process and AY-04 process

| Step Name | Protein A Process | | AY-04 |
| --- | --- | --- | --- |
| | Run 1 | Run 2 | Mapping Data * |
| Harvest Filtrate | | | |
| Protein A Capture | 91.81 | 97.12 | 86~91% |
| Viral Inactive Filtration | 91.00 | 97.65 | 97~98% |
| Q Sepharose ™ CC | 93.87 | 95.91 | 88~101% |
| Phenyl Sepharose ™ CC | 91.57 | 96.63 | 87~91% |
| Overall Chromatography | 71.81 | 87.90 | 72~82% |

* Data from Tech-report ABC/TO R348

Host Cell Proteins (HCP) are the major impurities generated by CHO cells. Besides impurities carried in harvest material, Protein A may leach from the protein A resin matrix into the product pool as a process related impurity. A good process must demonstrate its ability to clear HCP and leachable Protein A.

HCP Clearance. Batch harvest material was applied to a MabSelect™ (2.6×20 cm) column. HCP levels in the eluate were measured as described above and compared to the Fractogel™ S eluate in an AY-04 process. The data demonstrated that MabSelect™ chromatography removed 99.9% HCP loaded and the Fractogel™ S chromatography of AY04 removed 88 ~93% HCP loaded. As expected, Protein A affinity resin had better HCP clearance capability than Fractogel™ S cation exchange resin.

Protein A Leachables. To detect Protein A leached from the resin matrix, a commercial ELISA kit (Cygnus Technologies, Inc) was used to determine Protein A content. The Protein A leached during the affinity step was approximately 6 ng/mg-antibody in the eluate. After fine purification with Q Sepharose™ and Phenyl HP, the leached protein A was significantly reduced to approximately 0.02 ng/mg.

SDS-PAGE. A denatured reducing SDS-PAGE was conducted to compare the intermediate differences between Protein A process and AY-04 process. 2 µg of antibody of each sample was loaded. No obvious difference is observed in the gel (FIG. 10).

MabSelect™ Elution pH Study. In the case of Protein A affinity resin, antibody is bound at neutral pH and eluted under acidic condition. Since low pH viral reduction/inactivation is very efficient and widely used in monoclonal antibodies purification processes, the viral reduction/inactivation step can be simplified by holding the acidic MabSelect™ eluate for a sufficient time. The effect of elution pH on antibody recovery yield and product quality were studied. Elution around pH 3.2 was selected as the MabSelect™ elution pH based on its highest recovery yield and acceptable product quality in terms of monomer percentage and total lysine variants.

FIG. 11 demonstrates that a yield of at least 90% was obtained for an elution pH range from 2.5 to 3.8 and a significant decrease in yield occurs at pH 4. This suggests that at an elution buffer pH higher than pH 4 could not sufficiently elute antibody from MabSelect™ resin.

Impact on Antibody Aggregation. All of antibody (Adalimumab) monomer levels in MabSelect™ eluates were higher than 92% (FIG. 12). They all met the in-process action limits (SEC HPLC monomer 92%) of Fractogel™ Chromatography in AY-04 process at an elution buffer pH range of 2.5 to 3.8, although higher elution pH generated less aggregates. Eluate holding time under acidic condition for 1 to 3 hours did not significantly affect antibody aggregation.

3. Determination of Host Cell Protein Concentration in Anti-IL-12 Antibody Compositions This procedure describes the testing methodology for the determination of residual Host Cell Protein concentration in anti-IL-12 antibody samples. Enzyme Linked Immunosorbent Assay (ELISA) is used to sandwich the Host Cell Protein (Antigens) between two layers of specific antibodies. This is followed by the blocking of non-specific sites with Casein. The Host Cell Proteins are then incubated during which time the antigen molecules are captured by the first antibody (Coating Antibody). A second antibody (anti-Host Cell Protein Biotinylated) is then added which fixes to the antigen (Host Cell Proteins). Neutravidin HRP-conjugated is added which binds to the Biotinylated anti-Host Cell Protein. This is followed by the addition of K blue substrate. The chromogenic substrate is hydrolyzed by the bound enzyme conjugated antibody, producing a blue color. Reaction is stopped with 2M $H_3PO_4$, changing color to yellow. Color intensity is directly proportional to the amount of antigen bound in the well.

Preparation of 50 mM Sodium Bicarbonate (Coating Buffer), pH 9.4. To a 1 L beaker add: 900 mL Milli-Q water; 4.20 g±0.01 g Sodium Bicarbonate. Stir until completely dissolved. Adjust pH to 9.4 with 1 N NaOH. Transfer to a 1 L volumetric flask and bring to volume with Milli-Q water. Mix by inversion until homogeneous. Filter through a 0.22 µm sterile filter unit. Store at nominal 4° C. for up to 7 days from the date of preparation. Preparation of 0.104 M $Na_2HPO_4*7H_2O$, 1.37 M NaCl, 0.027 M KCl, 0.0176 M $KH_2PO_4$, pH=6.8-6.9 (10×PBS). Add approximately 400 mL of Milli-Q water to a glass beaker. Add 13.94 g±0.01 g of $Na_2HPO_4x7H_2O$. Add 40.0 g±0.1 g of NaCl. Add 1.00 g±0.01 g of KCl. Add 1.20 g±0.01 g of $KH_2PO_4$. Stir until homogeneous. Transfer to a 500 mL volumetric flask. QS to 500 mL volume with Milli-Q water. Mix by inversion. Filter through a 0.2 µm sterile filter unit. Store at room temperature for up to 7 days.

Preparation of 1×PBS+0.1% Triton X-100, pH 7.40: (Plate Wash Buffer). In a 4 L graduated cylinder, mix 400 mL 10×PBS (step 5.2) with 3500 mL Milli-Q Water. Check pH, and adjust if necessary to 7.40±0.05 with 1 N HCl or 1 N NaOH. Bring to volume with Milli-Q water. Tightly parafilm the cylinder and mix by inversion until homogeneous. Transfer to a 4 L bottle. Remove 4 mL of the 1×PBS and discard. Add 4 mL of triton X-100 to the 3996 mL of 1×PBS. Place on stir plate and stir to completely dissolve. Filter the amount of plate wash buffer needed for dilution buffer preparation through a 0.22 µm sterile filter unit. Store at room temperature for up to 7 days.

Preparation of Coating Antibody Mixture: goat anti CHO 599/626/748 (lot #G11201 @ 1.534 mg/mL), affinity purified: NOTE: Stocks stored at nominal −80° C. in vials. Prepare aliquots. Take out one aliquot per plate at time of use. Immediately before use: Dilute antibody mixture to have a final concentration of 4 µg/mL in cold 50 mM Sodium Bicarbonate as follows. For example: add 31 µLs coating antibody mixture to 11969 µLs cold coating buffer. Mix gently by inversion.

Preparation of Biotinylated goat anti Host Cell Protein Mixture, 599/626/748 (lot#G11202 @ 0.822 mg/mL): NOTE: Stocks stored at nominal −80° C. in vials. Prepare aliquots. Take out one aliquot per plate at time of use. Immediately before use: dilute biotinylated antibody mixture to have a final concentration of 1 µg/mL in 37° C.±2° C. Casein as follows. For example: add 14.6 µLs biotinylated antibody mixture to 11985 µLs 37° C.±2° C. Casein. Mix gently by inversion.

Preparation of Neutravidin-HRP. Reconstitute new lots (2 mg/vial) to 1 mg/mL as follows: Add 400 µL of Milli-Q water to the vial, then add 1600 µL 1×PBS, for a total of 2 mL. Vortex gently to mix. Store at nominal −20° C. Prepare aliquots with desired volume so that 1 aliqout per plate is used. Prepare in polypropylene tube. Qualify new lots to determine working concentration. Assign expiry of 6 months from the date of preparation. For example, if the working concentration was determined to be 0.2 µg/mL then prepare as follows. Immediately before use: thaw an aliquot of Neutravidin-HRP at room temperature. Dilute the 1 mg/mL Neutravidin solution to 0.1 mg/mL (100 µg/mL) with 37° C.±2° C. Casein. For example: Dilute X10, add 50 µL of neutravidin to 450 µL of Casein. Vortex gently to mix. Further dilute the 100 µg/mL solution to 0.2 µg/mL with 37° C.±2° C. Casein. For example: Dilute X500, add 24 µL neutravidin (100 µg/mL) to 11976 µL of Casein. Vortex gently to mix.

Preparation of 5.7 2M Phosphoric Acid (Stop Solution). Prepare a 2 M Phosphoric acid solution from concentrated phosphoric acid as follows. From the % phosphoric acid stated on the label, density (1.685 g/mL) and formula weight (98 g/mole), calculate the volume of concentrated phosphoric acid needed to prepare 500 mL of 2M phosphoric acid. Add the volume of concentrated phosphoric acid calculated above to the flask. Bring to volume with Milli-Q water and mix by inversion until homogeneous. Store at ambient temperature for up to 6 months from the date of preparation.

Preparation of Dilution Buffer (Casein diluted X100 in 1×PBS+0.1% Triton X100, pH 7.4). Dilute 37° C.±2° C. Casein X100 in 0.22 µm sterile filtered 1×PBS+0.1% Triton X100, pH 7.4 (from above). For example: Add 1 mL of 37° C.±2° C. Casein to 99 mL 0.22 µm sterile filtered 1×PBS+0.1% Triton X100, pH 7.4. Mix well. Prepare fresh for each use.

Preparation of Standards. Host cell Protein Standards (Antigen Standards) (lot #G11203 @ 1.218 mg/mL): NOTE: Stocks stored at nominal −80° C. in 70 µL aliquots. Thaw an aliquot at room temperature. Perform serial dilutions in polypropylene tubes using Dilution buffer.

Preparation of Samples. In polypropylene tubes, dilute final bulk samples to 24 mg/mL in Dilution Buffer. Record concentration. NOTE: use the solutions below to prepare spiked samples and to prepare the 12 mg/mL solutions referenced below. In polypropylene microtubes, further dilute the 24 mg/mL solutions to 12 mg/mL in Dilution Buffer. Load triplicate wells for each of the 12 mg/mL solutions on the plate for a total of 6 wells. Preparation of Spike. In a polypropylene microtube, prepare a 10 ng/mL Host Cell Protein spike from the 20 ng/mL standard prepared above by diluting it 2× with Dilution Buffer. Load three wells for the 10 ng/mL spike solution onto the plate. Use the 20 ng/mL standard solution from step 6.1 for spiking samples.

Preparation of Spiked Samples. In polypropylene microtubes, spike 300 µL of each 24 mg/mL final bulk solution with 300 µL of the 20 ng/mL spike solution (6.1). Load triplicate wells for each spiked sample solution for a total of 6 wells.

Preparation of Control. A control range must be set for every new control stock solution, before use in routine testing. Control Stock: Prepare 150 µL aliquots of a batch of ABT-874 Drug Substance Concentrate and store frozen at nominal −80° C. for up to three years.

Preparation of Working Control. Thaw an aliquot of control at room temperature. In polypropylene tubes, dilute control to 24 mg/mL with Dilution Buffer. In polypropylene microtubes, further dilute the 24 mg/mL control solution with dilution buffer to 12 mg/mL. Prepare a single dilution and load control into 3 wells of the plate.

ELISA procedures. Fill plate wash bottle with plate wash buffer (refer to step 5.3, 1×PBS+0.1% Triton X-100). Prime plate washer. Check the following parameters: Parameters should be set to: Plate Type: 1 For each Cycle (a total of 5 cycles): Volume: 400 µls; Soak Time: 10 seconds; Asp. Time: 4 seconds.

Assay Procedure. Coat plates with 100 µL/well of 4 µg/mL goat coating antibody mixture in cold 50 mM Sodium Bicarbonate. Tap the side of the plate until the coating solution covers the bottom of the wells uniformly, cover with sealing tape and incubate at nominal 4° C. while shaking on plate shaker (or equivalent) at speed 3 for 18 hours±1 hour. After overnight incubation, remove plate from refrigerator and allow to equilibrate to room temperature. Shake out coating. Blot plate on paper towels. Block with 300 µL/well of 37° C.±2° C. Casein, cover with sealing tape and incubate at 37° C.±2° C. while shaking on Lab-line Environ plate shaker (or equivalent) at 80 rpm±5 rpm for 1 hour. Prepare standard, sample, control, spike, and spiked samples during blocking incubation. Wash the plate 5 times with Wash Buffer. Blot plate on paper towels. Using an 8-channel pipette, pipet 100 µL/well of standards, samples, spikes, spiked samples, and control into triplicate wells of the plate. Pipette 100 µL/well of Dilution Buffer into all empty wells of the plate to serve as blanks. Cover with sealing tape and incubate at 37° C.±2° C. while shaking on Lab-line Environ plate shaker (or equivalent) at 80 rpm±5 rpm for 1 hour. Fill out a template to use as a guide when loading plate.

Plate Reader Set-Up. Set up template, entering concentrations for standards. Do not enter dilution factors for samples, control, spike, or spiked samples. Assign the wells containing diluent as blanks to be subtracted from all wells. Wash the plate 5 times with Wash Buffer. Blot plate on paper towels. Add 100 µL/well biotinylated goat antibody. Cover with sealing tape and incubate at 37° C.±2° C. while shaking on Lab-line Environ plate shaker (or equivalent) at 80 rpm±5 rpm for 1 hour. Wash the plate 5 times with Wash Buffer. Blot plate on paper towels. Add 100 µL/well Neutravidin-HRP conjugate solution. Cover with sealing tape and incubate at 37° C.±2° C. while shaking on Lab-line Environ plate shaker (or equivalent) at 80 rpm±5 rpm for 1 hour. Wash the plate 5 times with Wash Buffer. Blot plate on paper towels. Add 100 µL/well cold K-Blue substrate, cover with sealing tape and incubate at room temperature for 10 minutes (start timer as soon as substrate is added to first row), while shaking speed 3 on Lab-line titer plate shaker (or equivalent). Stop the reaction by adding 100 µL/well 2M Phosphoric Acid (Step 5.7). Place plate on a plate shaker at speed 3 for 3-5 minutes. Read plate at 450 nm.

Data Analysis and Calculations. NOTE: only samples, spikes, spiked samples, and control, with optical densities falling within the practical quantitation limit (2.5 ng/mL standard) of the standard curve and meeting the % CV or % difference criteria stated below, are accepted. If sample OD's fall below the 2.5 ng/mL standard, result should be reported as less than 2.5 ng/mL. This value should then be divided by the diluted sample concentration (12 mg/mL) to report value in ng/mg. If sample is high in host cell concentration causing the non-spiked and/or the spiked sample to be above standard curve, report value as >100 ng/mL. This value should then be divided by the diluted sample concentration (12 mg/mL) to report value in ng/mg. Consider sample value zero for spike recovery calculations when the sample is below the 2.5 ng/mL standard.

Standard Curve. Standard concentrations should be entered into the protocol template. A quadratic curve fit is used. Coefficient of determination must be =0.99 and the %

CV between triplicate wells must be =20%. If this criteria is not met: One standard (1 level, 3 wells) may be dropped. If the 1.25 ng/mL is dropped, only samples and spiked samples with optical densities falling within the 2.5 ng/mL and 100 ng/mL (the remaining standard curve points) optical densities are acceptable. Additionally, for the triplicates of each standard level, if a single well is clearly contaminated or shows low binding, it may be dropped. If a well is dropped from a standard level, the remaining replicates must have a % difference=20%. The % CV for the lowest standard, which shows OD values close to the background (blanks) of the plate, should be =30%. If one well is dropped, the % difference for the remaining replicates must be =35%. If the lowest standard is dropped, only samples and spiked samples with optical densities falling within the remaining standard curve level optical densities are acceptable.

Samples. % CV should be =20% between triplicate wells. Report % CV between triplicate wells. One well from each sample dilution may be dropped. The remaining replicates must have a % difference of =20%. Note: if non-spiked sample OD is below the 2.5 ng/mL standard OD the % difference criteria does not apply to the non-spiked results. Refer to calculation above.

Calculate actual Host Cell Concentration in ng/mg from the mean (ng/mL) value as follows: CHO Host Cell Protein (ng/mg)=Mean "Non-spiked sample result (ng/mL)"_ Diluted sample concentration (12 mg/mL).

Spikes. % CV should be =20% between triplicate wells. Record % CV. One well from the spike may be dropped. The remaining points must have a % difference=20%. Refer to calculation in above. Report host cell concentration in ng/mL. This result will be used in spike recovery calculations. The resulting concentration for the spike (ng/mL) must be ±20% of the theoretical spike concentration. Record result and indicate Pass or Fail. If the spike result is not within 20% of theoretical, the assay must be repeated. Mean Spike Concentration (ng/mL)×100=must be 100%±20% 10 ng/mL.

Spiked Samples. % CV should be =20% between triplicate wells. Record % CV between triplicate wells. One well from each spiked sample dilution may be dropped. The remaining replicates must have a % difference of =20%. Refer to calculation above. Report "Spiked sample result" for each dilution in ng/mL. Record % difference between duplicate dilutions. The % difference between dilutions should be =25%. These results will be used in the spike recovery calculations.

Calculate % Spike Recovery for each dilution set using the formula below: % Spike Recovery=Spiked sample value–Non-Spiked Sample Value X 100 Spike Value. NOTE: (1) If non-spiked sample value OD's fall below the 2.5 ng/mL standard consider value as zero in % spike recovery calculation. % Spike recovery must be 100%±50% (50%-150%) for each dilution for each sample. Record results and Pass/Fail.

Control. % CV should be =20% between triplicate wells. Record % CV result. One well from the control may be dropped. The remaining replicates must have a % difference of=20%. Refer to calculation above. Report Host Cell concentration in the control in ng/mL. Calculate Host Cell concentration in ng/mg as follows: Host Cell Protein (ng/mg)=Control Host Cell Protein result in ng/mL.

4. Determination of Protein a Concentration in Anti-IL-12 Antibody Compositions

In this ELISA, plates are coated with Chicken Anti-Protein A and incubated. Non-specific sites are blocked with casein in PBS. Plates are washed in 1×PBS+0.1% Triton X-100 to remove unbound material. Samples and Cys-rproteinA standards are diluted in 1×PBS+4.1% Triton X+10% Casein. The solutions are denatured by heating at 95° C.±2° C., separating Protein A from ABT-874. The solutions are then added to the plate and incubated. Unbound material is washed off with 1×PBS+0.1% Triton X-100. Biotinylated Chicken Anti-Protein A is added to the microtiter plate and incubated. The plate is washed to remove unbound material and Neutravidin-Peroxidase conjugate is added.

The Neutravidin will bind to the Biotinylated Chicken Anti-Protein A that has bound to the wells. The plate is washed again to remove the unbound Neutravidin and K-Blue (tetramethylbenzidine (TMB)) substrate is added to the plate. The substrate is hydrolyzed by the bound Neutravidin producing a blue color. The reaction is stopped with Phosphoric Acid, changing color to yellow. The intensity of the yellow color in the wells is directly proportional to the concentration of Protein A present in the wells.

Preparation of Reagents and Solutions Casein bottles must be warmed to 37° C.±2° C.; sonicated for 2 minutes, and aliquoted. Aliquots are to be stored at nominal 4° C. When assay is to be run, the number of casein aliquots needed, should be placed at 37° C.±2° C. The coating buffer and substrate are used cold (taken from nominal 4° C. right before use).

50 mM Sodium Bicarbonate (Coating Buffer), pH 9.4. To a 1 L beaker add: 900 mL Milli-Q water 4.20 g±0.01 g Sodium Bicarbonate. Stir until completely dissolved. Adjust pH to 9.4 with 1 N NaOH. Transfer to a 1 L volumetric flask and bring to volume with Milli-Q water. Mix by inversion until homogeneous. Filter through a 0.22 CA μm sterile filter unit. Store at nominal 4° C. for up to 7 days from the date of preparation.

104 M $Na_2HPO_4*7H_2O$, 1.37 M NaCl, 0.027 M KCl, 0.0176 M $KH_2PO_4$, pH=6.8-6.9. (10×PBS): Add approximately 400 mL of Milli-Q water to a glass beaker. Add 13.94 g±0.01 g of $Na_2HPO_4x7H2O$. Add 40.0 g±0.1 g of NaCl. Add 1.00 g±0.01 g of KCl. Add 1.20 g±0.01 g of $KH_2PO_4$. Stir until homogeneous. Transfer to a 500 mL volumetric flask. QS to 500 mL volume with Milli-Q water. Mix by inversion. Filter through a 0.2 CA μm sterile filter unit. Store at room temperature for up to 7 days.

1×PBS+0.1% Triton X-100, pH 7.40: (Plate Wash Buffer). In a 4 L graduated cylinder, mix 400 mL 10×PBS (see above) with 3500 mL Milli-Q Water. Check pH, and adjust if necessary to 7.40±0.05 with 1 N HCl or 1 N NaOH. Bring to volume with Milli-Q water. Tightly parafilm the cylinder and mix by inversion until homogeneous. Transfer to a 4 L bottle. Remove 4 mL of the 1×PBS and discard. Add 4 mL of triton X-100 to the 3996 mL of 1×PBS. Place on stir plate and stir to completely dissolve. Store at room temperature for up to 7 days.

Chicken Anti-Protein A Coating Antibody. Take out one aliquot of antibody per plate at time of use. To qualify new lots of Chicken Anti-Protein A, it may be necessary to use and qualify Chicken Anti-Protein A-Biotin Conjugated (prepared from the same lot of coating) together. Immediately before use: Dilute antibody mixture in cold 50 mM Sodium Bicarbonate to the concentration determined during coating qualification. For example: If during qualification the concentration of coating to load on the plate was determined to be 6 μg/mL and if the stock concentration is 3000 μg/mL, then add 24 μLs coating antibody to 11976 μLs cold coating buffer. Mix gently by inversion.

Biotinylated Chicken anti Protein A. Take out one aliquot of antibody per plate at time of use. To qualify new lots of Chicken Anti-Protein A-Biotin Conjugated, it may be necessary to use and qualify it with the same lot of Chicken Anti-Protein A it was prepared from. Immediately before use: Dilute biotinylated antibody in 37° C.±2° C. Casein to the concentration determined during biotinylated antibody qualification. For example: If during qualification the concentration of biotinylated antibody to load on the plate was determined to be 4 µg/mL and if the stock concentration is 1000 µg/mL, then add 48 µLs biotinylated antibody to 11952 µLs 37° C.±2° C. Casein. Mix gently by inversion.

Neutravidin-HRP. Reconstitute new lots (2 mg/vial) to 1 mg/mL as follows: Add 400 µL of Milli-Q water to the vial, then add 1600 µL 1×PBS, for a total of 2 mL. Vortex gently to mix. Store at nominal −80° C. Prepare aliquots with desired volume so that 1 aliqout per plate is used. Prepare in polypropylene tube. Assign expiration date of 6 months from the date of preparation. For example, if the working concentration was determined to be 0.1 µg/mL then prepare as follows. Immediately before use, thaw an aliquot of Neutravidin-HRP at room temperature. Dilute the 1 mg/mL Neutravidin solution to 0.01 mg/mL (10 µg/mL) with 37° C.±2° C. Casein. For example: Dilute X10, add 50 µL of neutravidin to 450 µL of Casein. Vortex gently to mix, X10 again, add 100 µL of X10 neutravidin to 900 µL of Casein. Vortex gently to mix. Further dilute the 10 µg/mL solution to 0.1 µg/mL with 37° C.±2° C. Casein. For example: Dilute X100, add 120 µL neutravidin (10 µg/mL) to 11880 µL of Casein. Invert several times gently to mix.

Stop Solution (Purchased 1 N Phosphoric Acid is used.) Store at ambient temperature for up to 1 year from the date of receipt. Dilution Buffer (1×PBS+4.1% Triton X100+10% Casein, pH 7.4). Add 86 mL of 1×PBS+0.1% Triton X100, pH 7.4 (from Step 5.3) to a beaker or flask, add 4 mL of Triton X-100, and 10 mL of Blocker Casein in PBS, and stir to dissolve/mix. It may take 20 to 30 minutes to dissolve triton. This equals a 1×PBS+4.1% Triton X100+10% Casein, pH 7.4 solution. Filter through a 0.22 CA µm sterile filter unit. Prepare fresh for each use. This is enough for 1 plate.

Protein A Standards (Antigen Standards). NOTE: Stocks stored at nominal −20° C. in 70 µL aliquots. Thaw an aliquot on ice. Perform serial dilutions according to the examples in the table below polypropylene tubes using Dilution buffer (see above) using the concentration stated on the manufacturers COA: For example if COA states stock concentration is 2.1 mg/mL (2100000 ng/mL) then: Thaw samples on ice. In polypropylene microcentrifuge tubes, dilute final bulk samples to 20 mg/mL in Dilution Buffer (above). Perform 2 separate dilutions. Record concentration. Use the solutions below to prepare spiked samples and to prepare the 10 mg/mL solutions. For example: Conc. (mg/mL) Vol. µL of X mg/mL solution Vol. of diluent (µL) Serial Dilution From 120 stock sample. In polypropylene microcentrifuge tubes, further dilute the 20 mg/mL solutions to 10 mg/mL in Dilution Buffer.

Preparation of Spike. In a polypropylene microcentrifuge tube, prepare a 0.296 ng/mL Protein A spike from the 0.593 ng/mL standard prepared above in Step 6.1 by diluting it 2× with Dilution Buffer. Perform a single dilution. Triplicate wells for the 0.296 ng/mL spike solution will be loaded onto the plate. Use the 0.593 ng/mL standard solution from Step 6.1 for spiking samples.

Preparation of Spiked Samples. In polypropylene microcentrifuge tubes, spike 500 µL of each 20 mg/mL final bulk solution with 500 µL of the 0.593 ng/mL spike solution. Hold for denaturation. Triplicate wells for each spiked sample solution will be loaded on the plate for a total of 6 wells.

Preparation of Control. Obtain a lot of ABT-874 Drug Substance. Prepare 150 jut aliquots and store frozen at nominal −80° C. for three years from the date aliquoted.

Working Control: Thaw an aliquot of control on ice. In a polypropylene microcentrifuge tube, dilute control to 10 mg/mL with Dilution Buffer to have a final volume of 1000 µLs. Prepare a single dilution. Hold for denaturation. Triplicate wells of control will be loaded onto the plate.

Denaturation. For plate blanks, add 1000 µLs of dilution buffer to microcentrifuge tubes equal to the number of blanks that will be run on the plate. The caps of the tubes may be parafilmed to prevent them from popping open during heating or a second rack may be placed on top of them to keep caps closed. Heat standards, non-spiked samples, spiked samples, spike, blanks, and control, at 95° C.±2° C. for 15 minutes. Remove parafilm from tubes during cooling, if used. Allow to cool for 15 minutes, and centrifuge for 5 minutes at approximately 10000 rpm. Transfer 700 µLs of the supernatant into microtubes to load on plate. Be careful not to disturb the triton/protein pellet.

Plate Washer Instructions and Waterbath Set-Up. Fill plate wash bottle with plate wash buffer (refer to Step 5.3, 1×PBS+0.1% Triton X-100). Prime plate washer. Check the following parameters: Parameters should be set to: Plate Type: 1 For each Cycle (a total of 4 cycles): Asp speed: 10 mm/s; Volume: 4000s; Soak Time: 5 seconds; Asp. Time: 6 seconds. Turn on waterbath and set to 95° C. Allow waterbath temperature to equilibrate to 95° C.±2° C. for at least 30 minutes.

Assay Procedure: A Checklist can be used as a guide by checking off steps as they are completed. Additionally, record all equipment used during the assay. The amount of Casein aliquots to be used for each day the assay will be run must be placed at 37° C.±2° C. The coating Buffer and substrate are used cold. Prepare standard, sample, control, spike, and spiked samples prior to and during blocking incubation. It may take longer than the 1 hour block incubation to prepare dilutions, transfer to eppendorf tubes, denature for 15 minutes, cool for 15 minutes, centrifuge for 5 minutes, and to transfer to microtubes. Allow at least 40 minutes prior to blocking plates. Samples, Spiked Samples, Standards, Control, Assay Spike, and Blanks, are loaded on the plate horizontally from rows B through G using a 12 channel pipette. Standards are loaded from high to low concentration. Plate coating, biotin addition, neutravidin addition, substrate addition, and stop solution addition are done vertically from columns 2 through 11.

Coat plates with 100 µL/well of coating antibody in cold 50 mM Sodium Bicarbonate. Tap the side of the plate until the coating solution covers the bottom of the wells uniformly, cover with sealing tape and incubate at nominal 4° C. while shaking on plate shaker (or equivalent) at speed 3.

After overnight incubation, remove plate from refrigerator and allow to equilibrate to room temperature. Shake out coating. Blot plate on paper towels. Block with 300 µL/well of 37° C.±2° C. Casein, cover with sealing tape and incubate at 37° C.±2° C. while shaking on Lab-line Environ plate shaker (or equivalent) at 80 rpm±5 rpm for 1 hour±10 minutes.

Prepare standard, sample, control, spike, and spiked samples prior to and during blocking incubation. Wash the plate 4 times with Wash Buffer. Blot plate on paper towels. Using an 8-channel pipette, pipet 100 µL/well of denatured standards, samples, spikes, spiked samples, blanks, and control into triplicate wells of the plate. The outside wells of the plate are not used, add non-treated dilution buffer to these wells. Cover with sealing tape and incubate at 37° C.±2 C while shaking on Lab-line Environ plate shaker (or equivalent) at 80 rpm±5 rpm for 2 hours. Fill out a template to use as a guide when loading plate.

Plate Reader Set-Up. Wash the plate 4 times with Wash Buffer. Blot plate on paper towels. Add 100 µL/well biotinylated antibody. Cover with sealing tape and incubate at 37°

C.±2° C. while shaking on Lab-line Environ plate shaker (or equivalent) at 80 rpm±5 rpm for 1 hour.

Wash the plate 4 times with Wash Buffer. Blot plate on paper towels. Add 100 μL/well Neutravidin-HRP conjugate solution. Start timer as soon as neutravidin is added to the last row. Cover with sealing tape and incubate at 37° C.±2° C. while shaking on Lab-line Environ plate shaker (or equivalent) at 80 rpm±5 rpm for 30 minutes. Wash the plate 4 times with Wash Buffer. Blot plate on paper towels. Add 100 μL/well cold K-Blue substrate, cover with sealing tape and incubate at room temperature for 10 minutes (start timer as soon as substrate is added to first row), while shaking speed 3 on Lab-line titer plate shaker (or equivalent). Stop the reaction by adding 100 μL/well 1 N Phosphoric Acid. Place plate on a plate shaker at speed 3 for 3 minutes. Read plate at 450 nm.

Data Analysis and Calculations NOTE: Only samples, spikes, spiked samples, and control, with optical densities falling within the practical quantitation limit of the standard curve and meeting the % CV or % difference criteria stated below, are accepted. If sample OD's fall below standard curve, result should be reported as less than 0.18 ng/mL (assay LOQ). This value should then be divided by the diluted sample concentration (10 mg/mL) to report value in ng/mg. If the sample is high in Protein A concentration causing the non-spiked and/or the spiked sample to be above standard curve (2 ng/mL), then dilute further to be within the standard curve. This value should then be divided by the diluted sample concentration to report value in ng/mg. For spike recovery calculations, subtract non-spiked sample value (ng/mL) from spiked sample value (ng/mL) even when the non-spiked sample value (ng/mL) is below the curve. If value is negative or 'range' is obtained then consider non-spiked sample as zero for spike recovery calculations.

Standard Curve. Standard concentrations should be entered into the protocol template. A quadratic curve fit is used. Coefficient of determination must be =0.99 and the % CV between triplicate wells must be =20%. If this criteria is not met: One standard (1 level, 3 wells) may be dropped. If the 0.18 ng/mL is dropped, only samples and spiked samples with optical densities falling within the 0.26 ng/mL and 2 ng/mL (the remaining standard curve points) optical densities are acceptable. Additionally, for the triplicates of each standard level, if a single well is clearly contaminated or shows low binding, it may be dropped. If a well is dropped from a standard level, the remaining replicates must have a % difference=20%. The % CV for the lowest standard, which shows OD values close to the background (blanks) of the plate, should be =30%. If one well is dropped, the % difference for the remaining replicates must be =35%. If the lowest standard is dropped, only samples and spiked samples with optical densities falling within the remaining standard curve level optical densities are acceptable.

Calculate % Difference as follows: % Difference=(Abs. (result dilution 1-result dilution 2)/mean value)×100%. The assay must be repeated if the standards do not meet the above criteria. Report % CV and/or % difference values and standard Curve Coefficient of determination results.

Samples. % CV should be =20% between triplicate wells. Report % CV between triplicate wells. One well from each sample dilution may be dropped. The remaining replicates must have a % difference of =20%. Note: If non-spiked sample OD is below lowest standard OD the % difference criteria does not apply to the non-spiked results. Refer to calculation above.

Report "Non-spiked sample result" for each dilution in ng/mL. These values will be used in spike recovery calculations. Calculate the mean "Non-spiked sample result (ng/mL)" and the % difference between dilutions. Report results. % Difference between dilutions must be =25%. Calculate actual Protein A Concentration in ng/mg from the mean (ng/mL) value as follows: Protein A (ng/mg)=Mean "Non-spiked sample result (ng/mL)" Diluted sample concentration (10 mg/mL). Record result.

Spikes. % CV should be =20% between triplicate wells. Record % CV. One well from the spike may be dropped. The remaining points must have a % difference=20%. Refer to calculation above. Report protein A concentration in ng/mL. This result will be used in spike recovery calculations. The resulting concentration for the spike (ng/mL) must be ±20% of the theoretical spike concentration. Record result and indicate Pass or Fail. If the spike result is not within 20% of theoretical, the assay must be repeated. Mean Spike Concentration (ng/mL)×100=must be 100%±20% 0.296 ng/mL Spiked Samples. % CV should be =20% between triplicate wells. Record % CV between triplicate wells. One well from each spiked sample dilution may be dropped. The remaining replicates must have a % difference of =20%. Refer to calculation above. Report "Spiked sample result" for each dilution in ng/mL. Record % difference between duplicate dilutions. The % difference between dilutions should be =25%. These results will be used in the spike recovery calculations. Calculate % Spike Recovery for each dilution set using the formula below: % Spike Recovery=Spiked sample value−Non-Spiked Sample Value×100. Spike Value NOTE: For spike recovery calculations, subtract non-spiked sample value (ng/mL) from spiked sample value (ng/mL) even when the non-spiked sample value (ng/mL) is below the curve. If value is negative or 'range' is obtained then consider non-spiked sample as zero for spike recovery calculations. % Spike recovery must be 100%±50% (50%-150%) for each dilution for each sample. Record results and Pass/Fail.

Control. % CV should be =20% between triplicate wells. Record % CV result. One well from the control may be dropped. The remaining replicates must have a % difference of=20%.

Various publications are cited herein, the contents of which are hereby incorporated by reference in their entireties.

What is claimed is:

1. A process for purifying adalimumab from a fermentation harvest of a Chinese Hamster Ovary (CHO) cell culture expressing said adalimumab, said process comprising:
   a) binding adalimumab from said fermentation harvest to a Protein A resin,
   b) eluting the bound adalimumab at an elution pH of 3.6-4, and
   c) incubating the eluted adalimumab for 1 to 3 hours.

2. The process of claim 1, wherein said eluting is at an elution pH is 3.6.

3. The process of claim 1, wherein said eluting is at an elution pH of 3.7.

4. The process of claim 1, wherein said eluting is at an elution pH of 3.8.

5. The process of claim 1, wherein said eluting is at an elution pH of 4.

6. The process of claim 1, further comprising after said incubating, subjecting adalimumab to one or more further chromatographic separations, wherein said one or more further chromatographic separations comprise an ion exchange chromatography, a hydrophobic interactive chromatography or a combination thereof.

7. The process of claim 1, further comprising subjecting adalimumab to an ion exchange chromatography after said incubating.

8. The process of claim 7, wherein said ion exchange chromatography is cation exchange chromatography.

9. The process of claim 7, wherein said ion exchange chromatography is anion exchange chromatography.

10. The process of claim 1, further comprising subjecting adalimumab to a hydrophobic interaction chromatography after said incubating.

11. The process of claim 1, further comprising determining the monomer level of adalimumab purified according to said process.

12. The process of claim 1, wherein the adalimumab monomer level after said incubating is greater than 97%.

13. The process of claim 1, wherein the purified adalimumab is pharmaceutical grade.

* * * * *